(12) United States Patent
Schwarz et al.

(10) Patent No.: US 8,072,537 B2
(45) Date of Patent: Dec. 6, 2011

(54) IMAGE PICK-UP MODULE

(75) Inventors: Peter Schwarz, Tuttlingen (DE); Christian Graf, Emmingen-Liptingen (DE); Klaus M. Irion, Emmingen-Liptingen (DE)

(73) Assignee: Karl Storz GmbH & Co. KG (DE)

( * ) Notice: Subject to any disclaimer, the term of this patent is extended or adjusted under 35 U.S.C. 154(b) by 523 days.

(21) Appl. No.: 12/175,804

(22) Filed: Jul. 18, 2008

(65) Prior Publication Data
US 2009/0021618 A1    Jan. 22, 2009

(30) Foreign Application Priority Data

Jul. 18, 2007 (DE) .......................... 10 2007 034 704

(51) Int. Cl.
*H04N 5/225* (2006.01)
*H04N 13/00* (2006.01)
*A61B 1/04* (2006.01)
(52) U.S. Cl. ........................... 348/374; 348/45; 348/373
(58) Field of Classification Search .................... 348/45, 348/65–75, 374
See application file for complete search history.

(56) References Cited

U.S. PATENT DOCUMENTS

| | | | |
|---|---|---|---|
| 4,745,471 A | | 5/1988 | Takamura et al. |
| 4,779,130 A | * | 10/1988 | Yabe ................................ 348/76 |
| 4,831,456 A | * | 5/1989 | Takamura ...................... 348/374 |
| 5,220,198 A | | 6/1993 | Tsuji |
| 5,454,366 A | * | 10/1995 | Ito et al. ........................ 600/109 |
| 5,754,313 A | | 5/1998 | Pelchy et al. |
| 5,857,963 A | | 1/1999 | Pelchy et al. |
| 6,142,930 A | | 11/2000 | Ito et al. |
| 7,683,960 B2 | * | 3/2010 | Minami et al. ................ 348/340 |
| 7,787,939 B2 | * | 8/2010 | Jacobsen et al. ............... 600/476 |
| 2002/0059721 A1 | * | 5/2002 | Crudo et al. ..................... 29/829 |
| 2002/0080223 A1 | | 6/2002 | Connor |

(Continued)

FOREIGN PATENT DOCUMENTS

DE    19924189 C2    1/2001

(Continued)

OTHER PUBLICATIONS

Japanese Office Action (translation); Application No. JP 2008-182755; Jul. 29, 2010; 3 pages.

(Continued)

*Primary Examiner* — Sinh Tran
*Assistant Examiner* — Christopher K Peterson
(74) *Attorney, Agent, or Firm* — St. Onge Steward Johnston & Reens LLC

(57) ABSTRACT

An image pick-up module, in particular for an endoscope or a miniature camera, has an electronic image sensor, which has a plurality of contact fingers that are arranged in at least one row, and a rigid circuit board to which the contact fingers are electrically contact-connected, the image sensor and the circuit board being arranged approximately parallel to one another, and the contact fingers extending along at least one longitudinal side of the circuit board, which extends approximately transversely to the image sensor, and also a flexible multi-core cable which leads from the circuit board in the direction away from the image sensor and whose cores are likewise electrically contact-connected to the circuit board. The cores are contact-connected at contact-connection points on the circuit board which are closer to the image sensor than that side of the circuit board which is remote from the image sensor.

5 Claims, 16 Drawing Sheets

U.S. PATENT DOCUMENTS

| | | | |
|---|---|---|---|
| 2002/0080233 A1* | 6/2002 | Irion et al. | 348/65 |
| 2004/0263680 A1 | 12/2004 | Sonnenschein et al. | |
| 2005/0195323 A1* | 9/2005 | Graham | 348/374 |
| 2006/0109368 A1* | 5/2006 | Ayrenschmalz | 348/340 |
| 2006/0180902 A1* | 8/2006 | Li et al. | 257/666 |
| 2007/0158773 A1 | 7/2007 | Cheng | |

FOREIGN PATENT DOCUMENTS

| | | |
|---|---|---|
| DE | 102004056946 A1 | 5/2006 |
| JP | 2000092477 A | 3/2000 |
| JP | 2000209472 A | 7/2000 |
| JP | 2001178675 A | 7/2001 |
| JP | 2002131656 A | 5/2002 |
| JP | 2002325728 A | 11/2002 |
| JP | 2005334509 A | 12/2005 |

OTHER PUBLICATIONS

European Search Report, EP08011821, Oct. 24, 2008, 6 pages.
German Search Report, May 29, 2008, 4 Pages.

\* cited by examiner

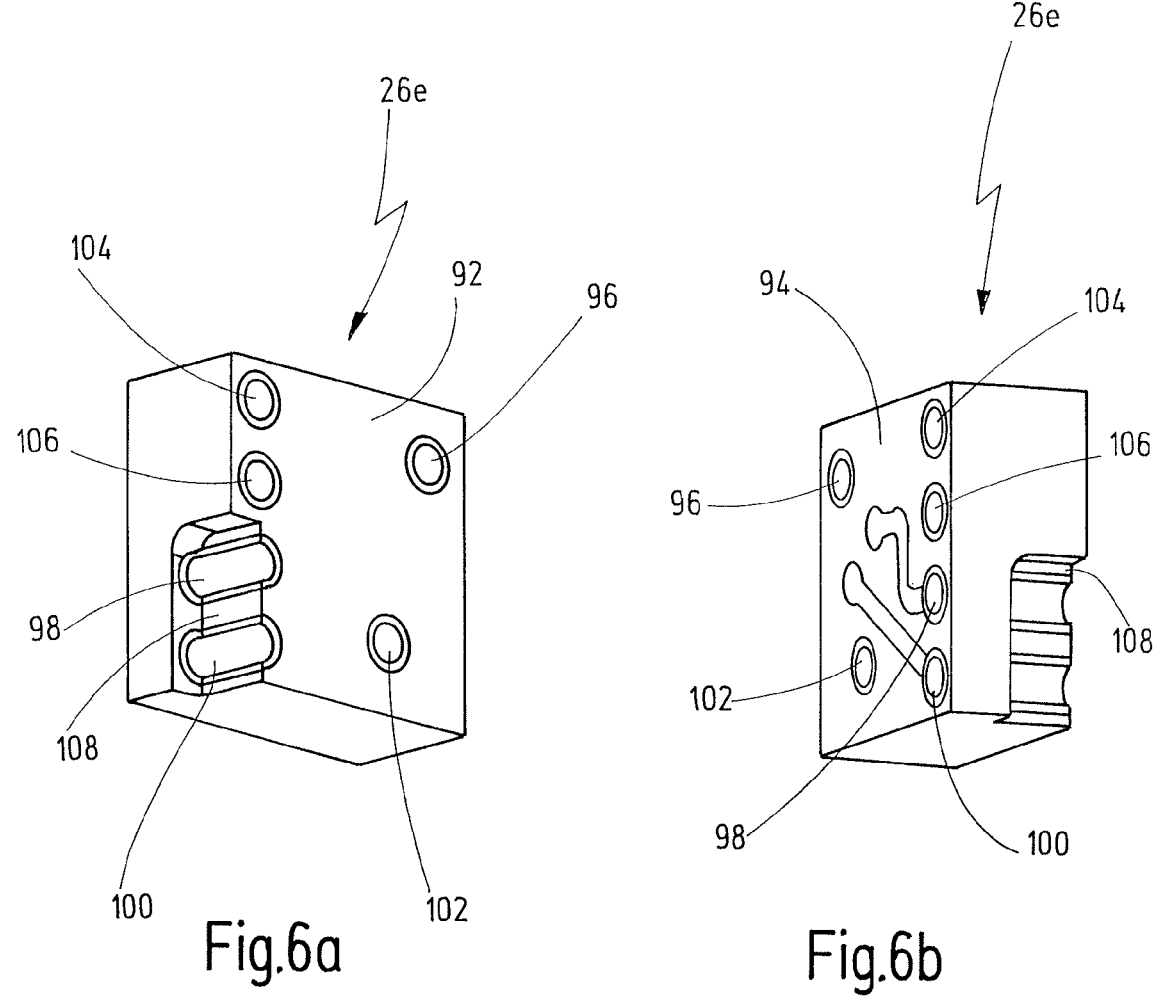

IMAGE PICK-UP MODULE

CROSS REFERENCE TO RELATED APPLICATION

The present application claims priority of German patent application No. 10 2007 034 704.0 filed on Jul. 18, 2007.

BACKGROUND OF THE INVENTION

The invention generally relates to image pick-up modules. More specifically, the invention relates to image pick-up modules for use in endoscopes or miniature cameras.

Without restricting generality, such an electronic image pick-up module is used in an endoscope, in particular in a flexible endoscope, the image pick-up module being arranged at the distal end of the endoscope shaft. Such an endoscope or video endoscope is disclosed, for example, in U.S. Pat. No. 5,754,313.

An image pick-up module generally comprises an electronic image sensor or image pick-up which converts light incident on it into an electrical signal. Such electronic image sensors are generally embodied using CCD or CMOS technology.

Miniaturized image sensors are currently available, of which those which have been produced using TAB (Tape Automated Bonding) technology are preferred. Such image sensors have contact fingers which are arranged in at least one row, usually in two rows on opposite sides of the image sensor, extend away from the image sensor approximately perpendicular to the light entry surface of the image sensor and are contact-connected to the circuit board of the image pick-up module. The contact fingers of an image sensor produced in TAB form are on the same plane as the image sensor. The contact fingers are bent over and are approximately perpendicular to the light entry surface of the image sensor only after they have been bent around.

In the sense of the present invention, a "circuit board" is understood as meaning both integral, single-part and multi-piece or multi-part circuit boards, particular ones of these designs being preferred in particular configurations, as also described below.

The circuit board (printed circuit board) is used not only to contact-connect the contact fingers of the image sensor but also to accommodate electronic components which are required for the control electronics and/or drive system of the image sensor.

A flexible multi-core cable which is used to guide the electrical video signals generated by the image sensor to the camera control unit and to supply drive and supply signals to the circuit board is also contact-connected to the circuit board.

The circuit board of an image pick-up module disclosed in the document DE 10 2004 056 946 A1 is of integral and rigid design and has the shape of a U, the U-shaped configuration being produced by milling material from a cuboidal or parallelepipedal circuit board blank. In accordance with the U-shaped configuration, this circuit board is open on two opposite longitudinal sides and closed on the remaining two opposite longitudinal sides. In the present description, "longitudinal direction" denotes the direction perpendicular to the light entry surface of the image sensor. Electrical components in a three-dimensional arrangement are contact-connected to the circuit board in that groove in the circuit board of the known image pick-up module which is formed by the U-shaped form, that is to say a plurality of electronic components are stacked on top of one another.

In this case, the multi-core flexible cable is contact-connected to the circuit board on the outer side of the circuit board which is remote from the image sensor and is referred to as the "underside" of the circuit board below. Although the known image pick-up module is very short in the longitudinal direction as desired, the contact-connection of the multi-core cable on the outer side of the circuit board which is remote from the image sensor has the disadvantage that the rigid part of the image pick-tip module, which is rigid overall, is extended in an undesirable manner by the cable assembly which has been contact-connected because the contact-connection points of the cores of the multi-core cable form a rigid arrangement which extends away from said outer side of the circuit board towards the proximal end.

In particular, when this image pick-up module is used in an endoscope having a flexible shaft, this results in the rigid distal beak part of the flexible endoscope being unfavourably extended. When the known image pick-up module is used, the rigid beak part of the flexible endoscope must be disadvantageously longer.

This known image pick-up module also has the disadvantage that the electronic or electrical components are arranged in the groove on top of one another rather than on one plane for reasons of space. As a result, a large amount of time and high costs are required when wiring the three-dimensionally arranged components and consequently when producing the entire image pick-up module.

DE-A-199 24 189 describes an image pick-up module whose circuit board is formed from a single-part plate which can be folded along flexible connecting sections and can be folded to form a parallelepipedal body having an essentially U-shaped cross section. When folded, the circuit board body has two sections, which extend essentially transversely to the image sensor and are spaced apart from one another, and a third section which runs essentially parallel to the image sensor, the image sensor being fitted to that end of the first and second sections of the circuit board body which is at a distance from the third section.

An image pick-up module disclosed in U.S. Pat. No. 5,754,313 has two separate circuit boards, the two circuit boards accommodating electronic miniature components and being used to contact-connect the cable or cable system which leads away. The two circuit boards run parallel to one another and approximately at right angles to the surface of the image sensor. The intermediate space between the two individual circuit boards is filled with a curable insulating filling composition and the multi-core cable is contact-connected on the outer sides of the two circuit boards. Both in the image pick-up module disclosed in DE 199 24 189 C2 and in the image pick-up module disclosed in U.S. Pat. No. 5,754,313, the circuit boards extend perpendicular to the image sensor, with the result that the circuit boards of these known image pick-up modules have a very long axial length which, as mentioned above, is undesirable, however.

The same applies to an image pick-up module which is disclosed in U.S. Pat. No. 5,857,963 and whose circuit boards or circuit board parts extend perpendicular to the image sensor. U.S. Pat. No. 5,220,198 discloses another image pick-up module which is comparable thereto and in which the circuit board is flexible and extends perpendicular to the image sensor.

U.S. Pat. No. 6,142,930 discloses an image pick-up module having a flexible circuit board, the cores of the multi-core cable being contact-connected on the outer side or underside of the circuit board which is remote from the image sensor, as a result of which the abovementioned disadvantages of the rigid part of the image pick-up module being extended exist.

Another disadvantage of all of the abovementioned image pick-up modules is the difficult assembly, that is to say the contact-connection of electronic components to the circuit board and the integration of electronic components on or in the circuit board.

SUMMARY OF THE INVENTION

The invention is based on the object of developing an image pick-up module of the type mentioned initially to the effect that, with a simultaneously compact design of the image pick-up module with a rigid circuit board which extends parallel to the image sensor, the contact-connection of the multi-core cable does not result in the image pick-up module being rigidly connected in the longitudinal direction.

According to an aspect of the invention, an image pick-up module is provided, comprising an electronic image sensor having a plurality of contact fingers that are arranged in at least one row, a rigid circuit board to which the contact fingers are electrically contact-connected, the image sensor and the circuit board being arranged approximately parallel to one another, and the contact fingers extending along at least one longitudinal side of the circuit board, which longitudinal side extends approximately transversely to the image sensor, and a flexible multi-core cable leading from the circuit board in direction away from the image sensor, wherein cores of the multi-core cable are electrically contact-connected to the circuit board at contact-connection points on the circuit board which are closer to the image sensor than a side of the circuit board which is facing away from the image sensor.

Like the known image pick-up module mentioned initially, the image pick-up module according to the invention thus has a rigid circuit board which is arranged parallel to the image sensor, as a result of which, in contrast to the additional image pick-up modules disclosed in the prior art, the overall length remains short in the longitudinal direction. However, in contrast to the known image pick-up module mentioned initially, the multi-core cable is not contact-connected on that side or underside of the circuit board which is remote from the image sensor but rather the contact-connection points are closer to the image sensor than that side or underside of the circuit board which is remote from the image sensor. As a result, the individual cores of the multi-core cable can completely deploy their flexibility at the level of that side of the circuit board which is remote from the image sensor, as a result of which the arrangement of the circuit board and image sensor on that side of the circuit board which is remote from the image sensor can be flexibly moved relative to the multi-core cable. In the case of coaxial cables as the multi-core cables, it is the inner conductors which are contact-connected at the abovementioned contact-connection points on the circuit board, while the outer conductors or the screens can be contact-connected at other points. When the image pick-up module according to the invention is used in a flexible endoscope, the distal beak part can therefore be short, the rigid contact-connection of the multi-core cable to the circuit board no longer having to be included in the length of the beak part.

In the image pick-up module disclosed in U.S. Pat. No. 5,754,313, although the multi-core cable is contact-connected approximately halfway up the circuit board as seen in the longitudinal direction, this circuit board is flexible in the initial state and only becomes rigid as a result of being filled with a curable filling composition. However, the process of contact-connecting the multi-core cable on flexible circuit boards or printed circuit boards is complicated from a production point of view and, as already mentioned, the circuit board of this known image pick-up module is very large in the longitudinal direction.

In one preferred configuration, the circuit board is of parallelepipedal design with four closed longitudinal sides, and the contact-connection points are situated on the outside of at least one, preferably two, of the longitudinal sides which is/are free of the contact fingers.

In this configuration, the contact fingers of the image sensor thus preferably extend on two opposite longitudinal sides of the parallelepipedal circuit board and the remaining two longitudinal sides are used to contact-connect the multi-core cable on the outside.

The individual cores of the multi-core cable are flexibly movable directly on that side or underside of the circuit board which is remote from the image sensor. This configuration has the advantage of a design of the image pick-up module which is very short in the longitudinal direction.

In this context, it is preferred if the circuit board has at least one blind hole, which accommodates at least one electronic component, between the four longitudinal sides.

This measure also contributes to the compact design of the image pick-up module according to the invention since the electronic component(s) for the control electronics and/or drive system and/or signal conditioning system of the image sensor can be accommodated in the blind hole in a space-saving manner without increasing the overall length of the image pick-up module in the longitudinal direction.

As an alternative to the abovementioned configurations, the circuit board may be of U-shaped design with two open and two closed longitudinal sides, the contact fingers extending along at least one of the open longitudinal sides and the contact-connection points of the cores being situated on at least one of the closed longitudinal sides.

Like the image pick-up module mentioned initially, the image pick-up module according to the invention can thus also be implemented with a U-shaped circuit board but, in contrast to the known image pick-up module, the contact fingers of the image sensor are not guided along the closed longitudinal sides of the circuit board but rather on the two open longitudinal sides, while the two closed longitudinal sides are then used to contact-connect the multi-core cable.

In the abovementioned configurations, the contact fingers preferably grip that side or underside of the circuit board which is remote from the image sensor and are contact-connected there, but contact-connection may also be effected on one longitudinal side or on two longitudinal sides of the circuit board.

In another preferred configuration, at least one longitudinally running depression for accommodating the cores is provided at least on the longitudinal sides on which the cores are contact-connected.

The advantage of this is that those cores of the multi-core cable which have been contact-connected on the outside do not increase the size of the cross section of the image pick-up module. In particular, it is not possible, in this configuration, for the circuit board including the cores of the cable to have a greater cross-sectional dimension than the image sensor itself. In addition, it is possible in this manner to produce an insulation spacing between the cores and a possible metal holder which accommodates the entire image pick-up module.

In another preferred configuration, the circuit board is of single-part design.

The advantage of this measure is that the circuit board can be produced in a simple manner and there are a small number of components in the image pick-up module.

The circuit board may also be in the form of a multilayer circuit board, that is to say the circuit board may be constructed from a plurality of layers each having conductor tracks, these conductor tracks preferably being connected to one another from layer to layer.

According to another aspect of the invention, an image pick-up module is provided, comprising an electronic image sensor, a rigid circuit board to which the electronic image sensor is electrically contact-connected, the image sensor and the circuit board being arranged approximately parallel to one another, wherein the circuit board is of multi-part design in the form of an arrangement of rigid individual circuit boards which run parallel to one another and parallel to the image sensor, and a flexible multi-core cable leading from the circuit board in direction away from the image sensor, wherein cores of the multi-core cable are electrically contact-connected to the circuit board at contact-connection points on the circuit board which are closer to the image sensor than a side of the circuit board which is facing away from the image sensor.

The advantage of a multi-part circuit board, which is constructed from individual circuit boards, over the single-part or integral U-shaped circuit board of the known image pick-up module mentioned initially is that each individual circuit board can be used to accommodate and contact-connect electronic components. In other words, starting from a parallel-epipedal circuit board, the latter is preferably split into two, or else optionally more, individual circuit boards which form a stacked arrangement in the longitudinal direction of the image pick-up module. In the case of the known image pick-up module, provision is made for electronic components to be stacked on top of one another in the U-shaped groove but this is difficult to achieve as regards the contact-connection of these components from a production point of view because some contact-connections have to be implemented using conductor wires which run freely in space, which can be carried out only with great difficulty and only by hand. In contrast, in the case of the present configuration, each individual circuit board can accommodate, for example, one electronic component which can then be directly contact-connected on the individual circuit board without the need for "three-dimensional" contact-connection.

In this case, it is also preferred if the individual circuit boards are connected to one another by means of the contact fingers of the image sensor or individual conductors or conductor tracks.

In this context, it is likewise preferred if the individual circuit boards have depressions in the form of grooves and/or blind holes for accommodating electronic components.

In this case, it is advantageous that the electronic components can be accommodated in the depressions in a space-saving manner, with the result that the individual circuit boards can then be stacked on top of one another in the longitudinal direction without a spacing or with only a slight spacing.

In another preferred configuration, the contact-connection points of the cores are situated on a side of the last individual circuit board, as seen from the image sensor, which faces the image sensor.

In this configuration, the last individual circuit board is therefore primarily used as the cable terminal, while the one or more other individual circuit boards are then used to contact-connect electronic components. This distribution of the functions of cable assembly and component assembly among separate individual circuit boards reduces assembly complexity and makes assembly open to an automated process, in particular. After all of the individual circuit boards have been assembled, they need only be joined together and contact-corrected to the image sensor.

In another preferred configuration of this aspect, the contact-connection points of the cores are situated on the longitudinal side of the last individual circuit board which is remote from the image sensor, this longitudinal side being smaller than the transverse dimension of the image sensor.

In this case too, the last individual circuit board which is remote from the image sensor is used as the cable terminal for contact-connecting the multi-core cable, the reduction in the size or, synonymous thereto, the smaller cross-sectional dimension of the longitudinal side of this individual circuit board advantageously resulting in the total transverse dimension of the last individual circuit board and the cores of the cable not being greater than the remaining transverse dimension of the image pick-up module.

As already described above in connection with a integral or single-part circuit board, it is likewise preferred if, in the event of the circuit board being constructed from a plurality of individual circuit boards, at least one of the individual circuit boards is in the form of a multilayer circuit board.

In this case too, the advantage is a higher integration density and a resultant possible particularly compact design of the entire circuit board.

In another preferred configuration, the circuit board has throughplated holes from the side which is remote from the image sensor to the side which faces the image sensor.

This configuration is particularly advantageous if the circuit board is in the form of a multilayer circuit board since the throughplated holes can then be used to electrically contact-connect the individual circuit board layers to one another.

In the event of the circuit board being constructed from a plurality of individual circuit boards, the latter can preferably be connected to one another by means of the contact fingers of the image sensor, said contact fingers preferably gripping that side of the last individual circuit board which is remote from the image sensor, as a result of which the individual circuit boards are also held together mechanically by means of the contact fingers.

According to still another aspect of the invention, an image pick-up module is provided, comprising an electronic image sensor, a rigid circuit board to which the image sensor is electrically contact-connected, the image sensor and the circuit board being arranged approximately parallel to one another, and a flexible multi-core cable leading from the circuit board in direction away from the image sensor, wherein cores of the multi-core cable are electronically contact-connected to the circuit board at contact-connection points on the circuit board which are closer to the image sensor than a side of the circuit board which is facing away from the image sensor, the contact-connection points of the cores are situated on a side of the circuit board which faces the image sensor, and the cores are guided through the circuit board from the side which is facing away from the image sensor to the side which faces the image sensor.

As a result of this configuration as well, the contact-connection points of the cores of the multi-core cable are closer to the image sensor than that side or underside of the circuit board which is remote from the image sensor, thus achieving the advantages described above. The additional advantage of this measure is that the transverse dimension of the circuit board is not increased by the cores without depressions for accommodating the cores having to be provided on the outer side.

As part of another configuration of the abovementioned measure, the circuit board is preferably at a distance from the image sensor.

As a result of the fact that the image sensor is at a distance from the circuit board, sufficient space is available for the contact-connection points of the cores on that side or top side of the circuit board which faces the image sensor. In particular, the cores with their screens may be guided through the circuit board, the exposed wire ends of the cores being bent over in a U-shaped manner towards the top side of the circuit board in order to be contact-connected to the top side of the circuit board.

In another preferred configuration, at least one electronic component is arranged in the space between the image sensor and the circuit board.

In this case, it is advantageous that the circuit board itself does not have to be provided with depressions as described above, thus saving a working step, namely the working step of milling depressions into the circuit board.

In this case, it is also preferred if the space between the circuit board and the image sensor is filled with a curable electrically insulating filling material.

In this case, it is advantageous that the filling material provides protection for the electronic components between the image sensor and the circuit board.

As part of the abovementioned configurations, it is also preferred if the contact fingers of the image sensor are contact-connected on at least one longitudinal side of the circuit board on which elongate contacts which are arranged so as to be recessed are provided.

In this case too, the advantage is again that the contact fingers can be contact-connected to the circuit board without increasing the cross-sectional dimensions of the image pick-up module on account of the depressions, the elongate contacts also being able to be used to connect conductor tracks to one another in an electrically conductive manner on that side of the circuit board which faces the image sensor as well as on that side of the circuit board which is remote from the image sensor, as a result of which advantageous use can be made of the three-dimensional structure of the circuit board.

According to still another aspect, an image pick-up module is provided, comprising an electronic image sensor, a rigid circuit board to which the image sensor is electrically contact-connected, the image sensor and the circuit board being arranged approximately parallel to one another, a flexible multi-core cable leading from the circuit board in direction away from the image sensor, wherein cores of the multi-core cable are electrically contact-connected to the circuit board at contact-connection points on the circuit board which are closer to the image sensor than a side of the circuit board which is facing away from the image sensor, the circuit board having a rigid base board which is used to contact-connect the multi-core cable, and at least one first further circuit board part which at least partially extends approximately perpendicular to the base board being flexibly connected to the base board.

In this configuration, the base board is primarily used to contact-connect the multi-core cable, to be precise on that side of the base board which faces the image sensor, as already described above, in order to ensure that the image pick-up module is not rigidly extended. On account of the at least one further circuit board part, the base board can be designed to be just so thick in the longitudinal direction that it is rigid in order to be able to contact-connect the multi-core cable in a simple manner from a production point of view. The at least one further circuit board part which at least partially extends approximately perpendicular to the base board can then be used to fasten and contact-connect at least one electronic component, as provided for in another preferred configuration.

As a result of the fact that the at least one further circuit board part is flexibly connected to the base board, the arrangement of the base board and the at least one further circuit board part can be spread out in a planar manner before the electrical components are contact-connected, as a result of which the electronic components can be fitted and contact-connected in automated fashion, in particular.

In another preferred configuration, the at least one first further circuit board part has at least one first section, which extends in an approximately perpendicular manner away from the base board towards the image sensor, and at least one second section which adjoins the first section and extends approximately parallel to the base board.

In this case, it is advantageous that the first section and the second section can bear and house electronic components, in particular if a third section is also provided, said third section running parallel to the first section in order to make optimum use of the space between the base board and the further circuit board part in conjunction with a simultaneously compact design.

In another preferred configuration of this aspect, the base board is flexibly connected to at least two further second and third circuit board parts which lead away from two opposite longitudinal sides of the base board perpendicular to the latter and enclose the multi-core cable.

In this case, it is advantageous that the multi-core cable is enclosed by the at least two further second and third circuit board parts such that it is protected, the flexible connection of the two further circuit board parts to the base board not being associated with any impairment of the flexibility of the image pick-up module from the underside of the base board. The two further second and third circuit board parts may have further conductor tracks and may also be used, in particular, to contact-connect the contact fingers of the image sensor on the outside.

In another preferred configuration, the base board and the at least one first and optionally at least one second and third further circuit board part are produced, together with the base board, from a circuit board blank, the base board having a greater material thickness than the further circuit board part(s).

In this case, it is advantageous that the entire circuit board comprising the base board and the further circuit board parts can first of all be spread out in a planar manner in order to contact-connect the electronic components, which makes contact-connection of the components open, in particular, to an automated process of loading and/or contact-connection, while, in the end, only the image sensor has to finally be applied to the circuit board which has been correspondingly folded into shape. However, in contrast to the foldable circuit boards which are disclosed in the prior art, the base board which is used as the cable terminal is rigid, which considerably simplifies the contact-connection of the multi-core cable. The greater material thickness of the base board in comparison with the further circuit board parts can be produced, for example, by removing the carrier material of the circuit board blank from the circuit board parts, with the exception of the base board, or conversely adding carrier material to the base board.

Further advantages and features emerge from the following description of the accompanying drawing.

It goes without saying that the features which have been mentioned above and are also to be explained below can be used not only in the respective combination stated but also in other combinations or on their own without departing from the scope of the present invention.

BRIEF DESCRIPTION OF THE DRAWINGS

Exemplary embodiments of the invention are illustrated in the drawing and are described in more detail below with reference to said drawing, in which:

FIGS. 6a)+b) show two different perspective views of a circuit board which can be used in an image pick-up module;

DETAILED DESCRIPTION OF PREFERRED EXEMPLARY EMBODIMENTS

FIGS. 1 to 5 and 7 to 10 illustrate different exemplary embodiments of image pick-up modules which are described in detail below.

All of the image pick-up modules shown are suitable, in particular, for installation in an endoscope, in particular a flexible endoscope, the image pick-up modules being suitable for installation in the distal tip of the shaft of such an endoscope, which is also referred to as the beak part, on account of their short axial length.

The image pick-up modules shown are optoelectronic assemblies in miniaturized Exemplary cross-sectional dimensions and lengths are in the range from 1 to 4 millimeters.

Figure 1A:
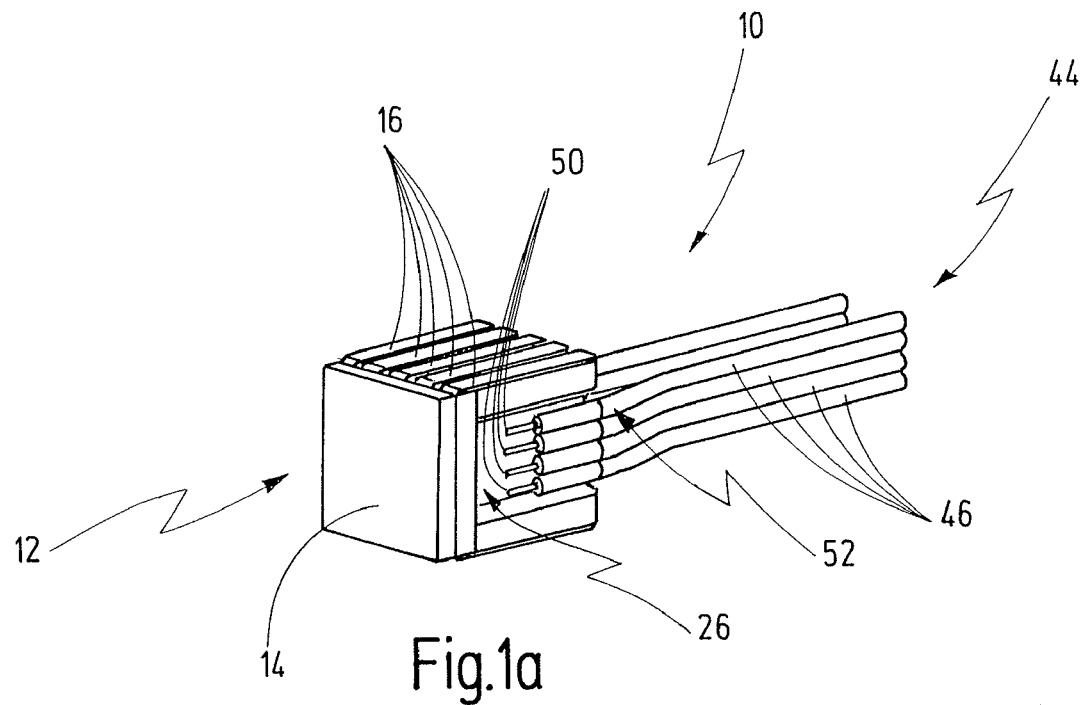
FIGS. 1a)+b) show a first exemplary embodiment of an image pick-up module, FIG. 1a) showing a perspective side view of the image pick-up module in the assembled state and FIG. 1b) showing an exploded view of the individual components of the image pick-up module.

FIGS. 1a) and b) show a first exemplary embodiment of an image pick-up module which is provided with the general reference symbol 10.

The image pick-up module 10 has an electronic image sensor 12 as a first main component. The image sensor 12 has an outer side 14 on the light entry side through which light enters the image sensor 12. During use of the image pick-up module 10, for example in the distal tip of an endoscope in the installed state, imaging optics are connected upstream of the outer side 14 on the light entry side in order to image an object to be observed on the image sensor 12.

The image sensor 12 is designed in a TAB configuration using CCD or CMOS technology.

The image sensor 12 has a plurality of contact fingers 16 and 18. In the exemplary embodiment shown, the image sensor 12 has a total of 10 contact fingers 16, 18. The contact fingers 16 and 18 are arranged in two rows on opposite sides 20 and 22 of a basic body 24 of the image sensor 12. In this case, the contact fingers 16 form a first row of contact fingers and the contact fingers 18 form a second row of contact fingers.

Another main component of the image pick-up module 10 is a circuit board 26 to which the contact fingers 16, 18 are electrically contact-connected in the assembled state of the image pick-up module 10 according to FIG. 1a).

In the exemplary embodiment shown, the circuit board 26 is of integral and single-part design. The circuit board 26 is also rigid. The circuit board 26 has a side 28 which faces the image sensor 12 and a side 30 which is remote from the image sensor 12. The circuit board 26 is generally parallelepipedal overall. The circuit board 26 also and 38 which are likewise opposite one another. The side 28 facing the image sensor 12 is oriented parallel to the image sensor 12 just like the side 30 remote from the image sensor 12. In the present description, the side 30 is also referred to as the underside of the circuit board 26.

The circuit board 26 is oriented parallel to the image sensor 12 overall, the sides 32 to 38 extending perpendicular to that outer side 14 of the image sensor 12 which defines the longitudinal direction of the image pick-up module 10.

Figure 1B:
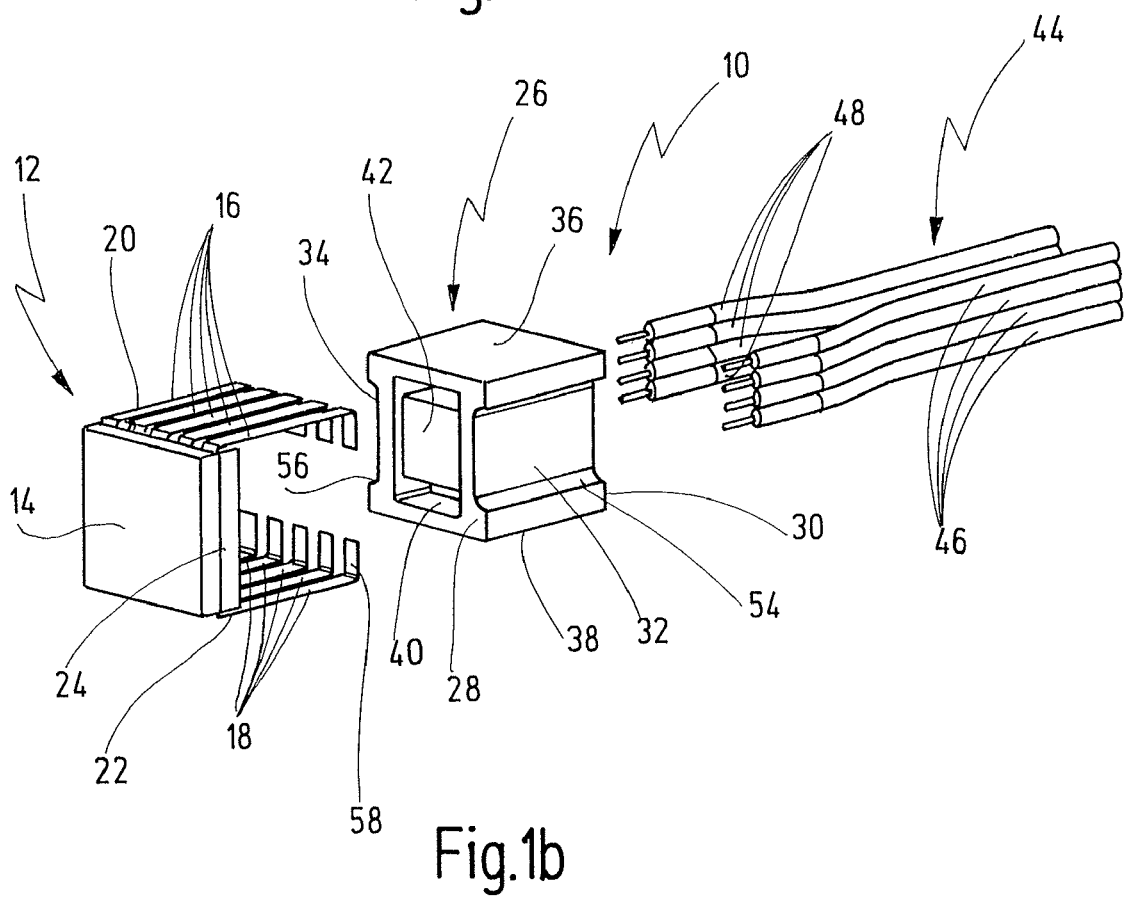

The circuit board 26 may be produced from a solid material. On the side 28 facing the image sensor 12, the circuit board 26 has a milled-out area in the form of a blind hole 40 between the four longitudinal sides 32 to 38. An electronic component 42 is arranged in the blind hole 40, a plurality of such electronic components also being able to be arranged in the blind hole 40. As illustrated in FIG. 1b), the component 42 is completely accommodated in the blind hole 40, that is to say it does not protrude beyond the side 28 of the circuit board 26, as a result of which the side 28 can be directly attached to the basic body 24 in the assembled state of the image pick-up module 10 in FIG. 1a).

The electronic component(s) 42 is/are part of control electronics for the image sensor 12.

The circuit board 26 has contact-connections (not illustrated) for contact-connecting the electronic component(s) 42.

The circuit board 26 is also used to contact-connect a multi-core cable 44 which has a total of eight cores 46, 48 in the exemplary embodiment shown.

The cores 46, 48 of the cable 44 are contact-connected to the circuit board 26 at contact-connection points 50 (as shown for the cores 46) which are closer to the image sensor 12 than that side or underside 30 of the circuit board 26 which is remote from the image sensor 12.

In this exemplary embodiment, the contact-connection points 50 are situated on the longitudinal sides 32 and 34 of the circuit board 26. On account of the fact that the contact-connection of the cores 46, 48 has been moved closer to the image sensor 12, rigid contact-connection points are avoided on the underside 30 of the circuit board 26, that is to say, in other words, the junction between the cores 46, 48 at a point 52 according to FIG. 1a) and the circuit board 26, that is to say directly on the underside of the circuit board 26, is flexible, which is advantageous, in particular, for installation of the image pick-up module 10 in the distal tip of a flexible endoscope because the distal tip or beak part of the flexible endoscope can have a very short axial length.

So that the cores 46 and 48 on the longitudinal sides 32 and 34 do not spread and do not exceed the transverse dimension of the image sensor 12 in these directions, corresponding depressions 54 and 56, in which the cores 46, 48 are accommodated, are made in the longitudinal sides 32 and 34. Instead of a single depression 54 for the four cores 46 and a single depression 56 for the four cores 48, individual depressions may also be provided for the individual cores 46, 48, as shown, for example, in the exemplary embodiment in FIG. 3.

As emerges from FIG. 1, the cores 46, 48 are contact-connected on the longitudinal sides 32 and 34 of the circuit board 26 which are free of the contact fingers 16, 18 of the image sensor 12. The contact fingers 16, 18 extend along the longitudinal sides 36, 38 of the circuit board 26 and grip the underside 30 of the circuit board 26 where they are preferably contact-connected. Ends 58 of the contact fingers 16, 18 are appropriately bent over the underside 30 of the circuit board 26.

Figure 2A:
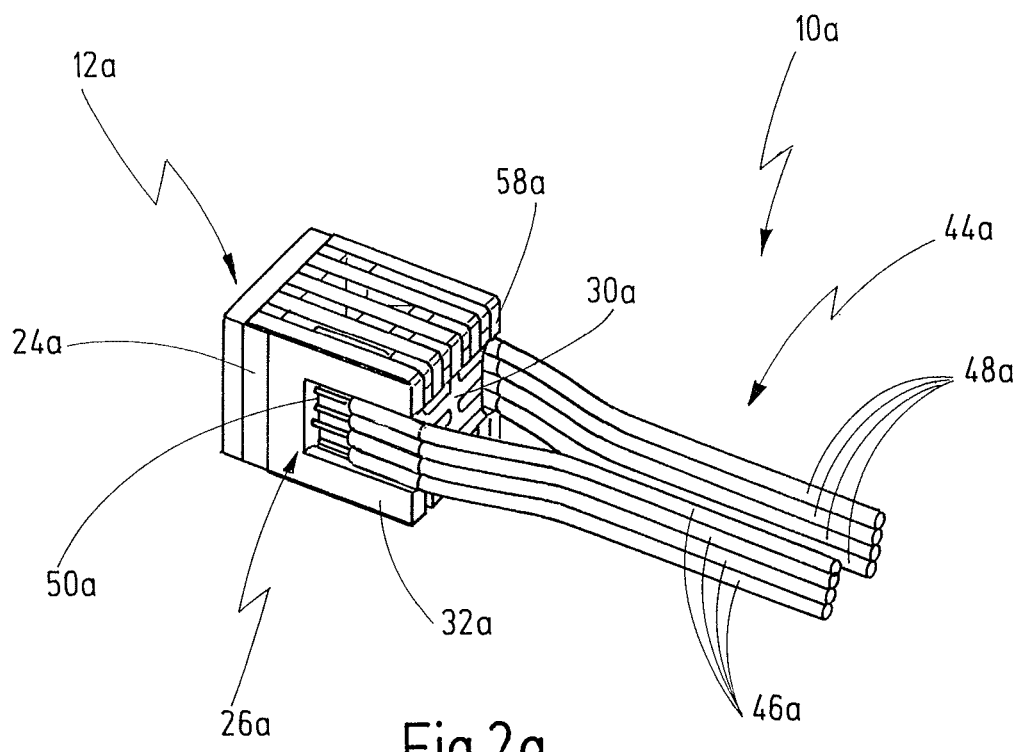
FIGS. 2a)+b) show another exemplary embodiment of an image pick-up module, FIG. 2a) showing a perspective side view of the image pick-up module in the assembled state and FIG. 2b) showing an exploded view of the individual components of the image pick-up module.

FIGS. 2a) and b) illustrate another exemplary embodiment of an image pick-up module 10a, individual parts of the image pick-up module 10a which are the same as or comparable to the corresponding parts of the image pick-up module 10 being provided with the same reference symbols supplemented by the letter a.

A description is primarily given below of the differences between the image pick-up module 10a and the image pick-up module 10. Unless stated otherwise, the description of the image pick-up module 10 applies to the image pick-up module 10a.

Although the circuit board 26a of the image pick-up module 10a is again of integral and single-part design like the circuit board 26, it has, in contrast to the circuit board 26, the shape of a U. The circuit board 26a correspondingly has a groove 60 which extends between two longitudinal sides 36a and 38a and is open on the longitudinal sides 36a and 38a.

Electronic components 42a and 42'a are arranged in the depression formed by the groove 60, to be precise in a three-dimensional arrangement, that is to say the components 42a and 42'a are arranged in the groove 60 such that they are stacked on top of one another, as described in DE 10 2004 056 946 A1, reference being made to that document as regards further details.

The cores 46a and 48a of the flexible multi-core cable 44a are contact-connected on the closed longitudinal sides 34a at contact-connection points 50a which are closer to the image sensor 12a than the underside 30a of the circuit board 26a. The contact fingers 16a and 18a of the image sensor 12a extend along the open longitudinal sides 36a and 38a of the circuit board 26a and their ends 58a are contact-connected on the underside 30a of the circuit board 26a.

Figure 2B:
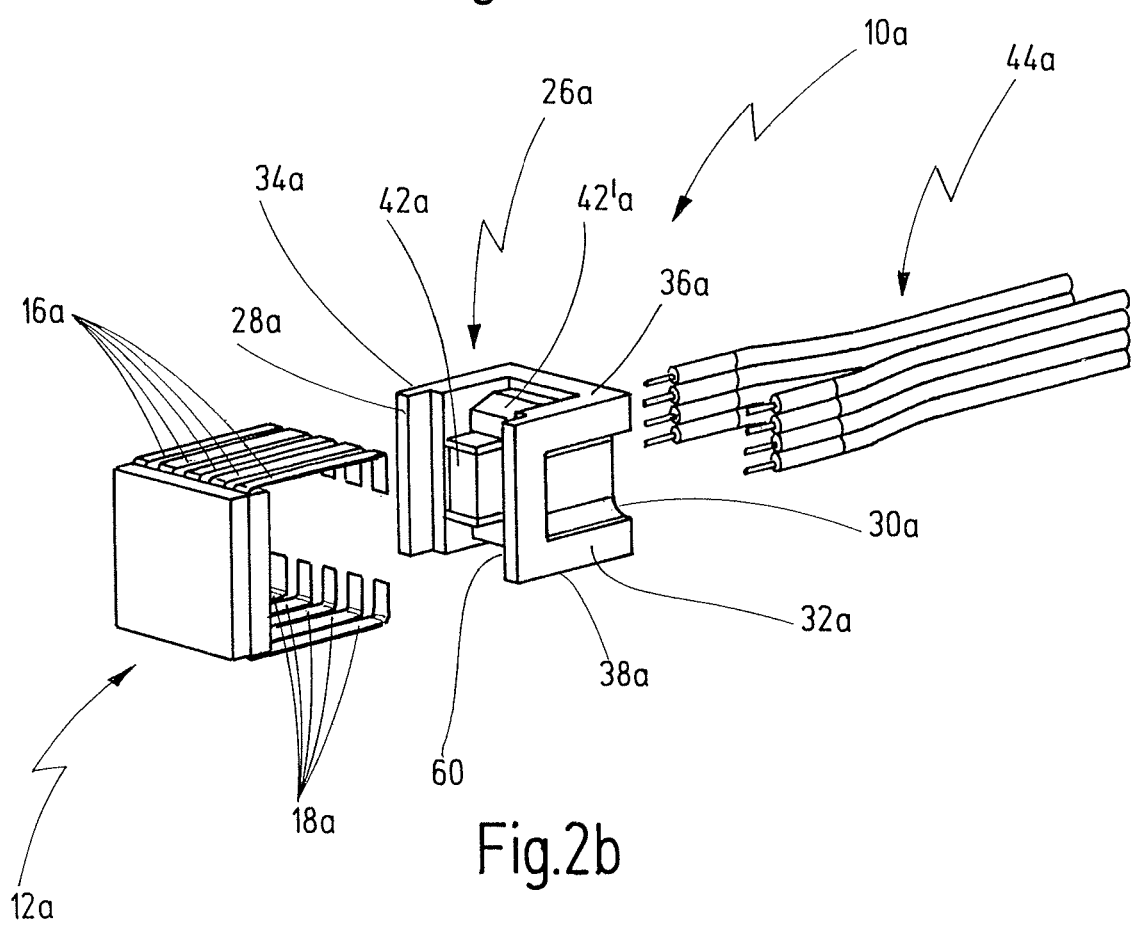
Figure 3A:
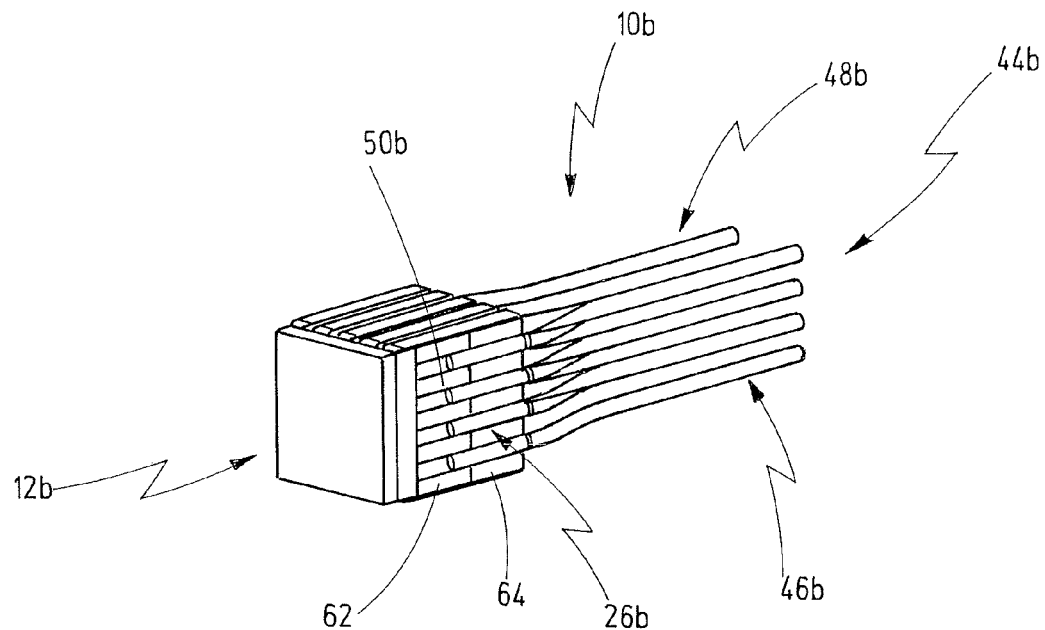
FIGS. 3a)+b) show another exemplary embodiment of an image pick-up module, FIG. 3a) showing a perspective side view of the image pick-up module in the assembled state and FIG. 3b) showing an exploded view of the individual components of the image pick-up module.
Figure 3B:
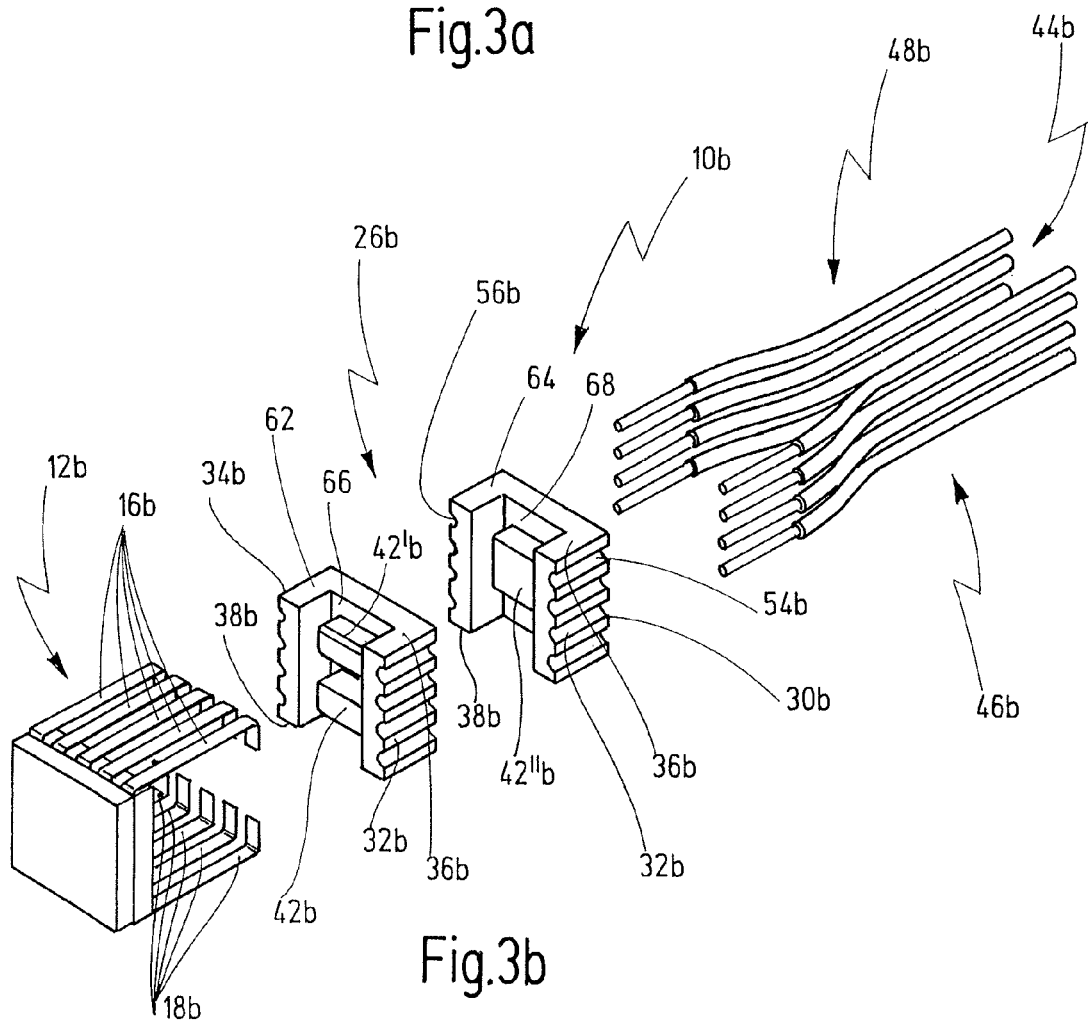

FIG. 3 shows another exemplary embodiment of an image pick-up module 10b which has been modified further in comparison with the exemplary embodiments in FIGS. 1 and 2. Parts of the image pick-up module 10b which are the same as or comparable to the corresponding parts of the image pick-up module 10 are provided with the same reference symbols supplemented by the letter b.

The image pick-up module 10b has a circuit board 26b which, in contrast to the circuit boards 26 and 26a, is of multi-part design rather than of integral and single-part design, to be precise the circuit board 26b is formed by an arrangement of rigid individual circuit boards 62 and 64 which run parallel to one another and are preferably joined together tightly such that they touch one another in the assembled state according to FIG. 3a).

In a manner comparable to the circuit board 26a, the individual circuit boards 62 and 64 are both of U-shaped design, but an embodiment of the individual circuit boards 62 and 64 with a blind hole as in the case of the circuit board 26 is also possible.

In the exemplary embodiment shown, both individual circuit boards 62 and 64 respectively accommodate one or more electronic components 42b, 42'b (individual circuit board 62) and 42"b (individual circuit board 64). In contrast to the circuit board 26a in which the components 42a, 42'a are arranged in the groove 60 of the circuit board 26a such that they are stacked on top of one another, the components 42b, 42'b and 42"b are respectively accommodated only in a "two-dimensional" arrangement in the individual circuit boards 62 and 64. The components 42b, 42'b and 42"b can thus be respectively mounted and contact-connected on a base 66 and 68 of the individual circuit boards 62, 64, as a result of which assembly of the individual circuit boards 62, 64 with the components 42b, 42'b, 42"b is easier than assembly of the circuit board 26a with the components 42a, 42'a.

The contact fingers 16b and 18b of the image sensor 12b are contact-connected on an underside 30b of the circuit board 26b, more precisely of the individual circuit board 64, which is remote from the image sensor 12b. The contact fingers 16b, 18b thus engage over the longitudinal sides 36b and 38b of the individual circuit boards 62, 64 and can be used, in particular, to hold the individual circuit boards 62 and 64 together.

The contact-connection points 50b of the cores 46b, 48b are situated on longitudinal sides 32b and 34b, which are free of the contact fingers 16h, 18h, such that they are displaced towards the image sensor 12b as seen from the underside 30b of the circuit board 26b, the cores 46b, 48b bridging the connecting point between the individual circuit boards 62, 64, as shown in FIG. 3a).

Furthermore, the individual circuit boards 62, 64 may also be electrically connected to one another by means of individual conductors or conductor tracks in order to increase the integration density of the circuit board 26b in the smallest possible space.

As a further difference to the image pick-up module 10 or 10a, the circuit board 26b of the image pick-up module 10b has separate depressions 54b and 56b for each of the cores 46b, 48b.

Figure 4A:
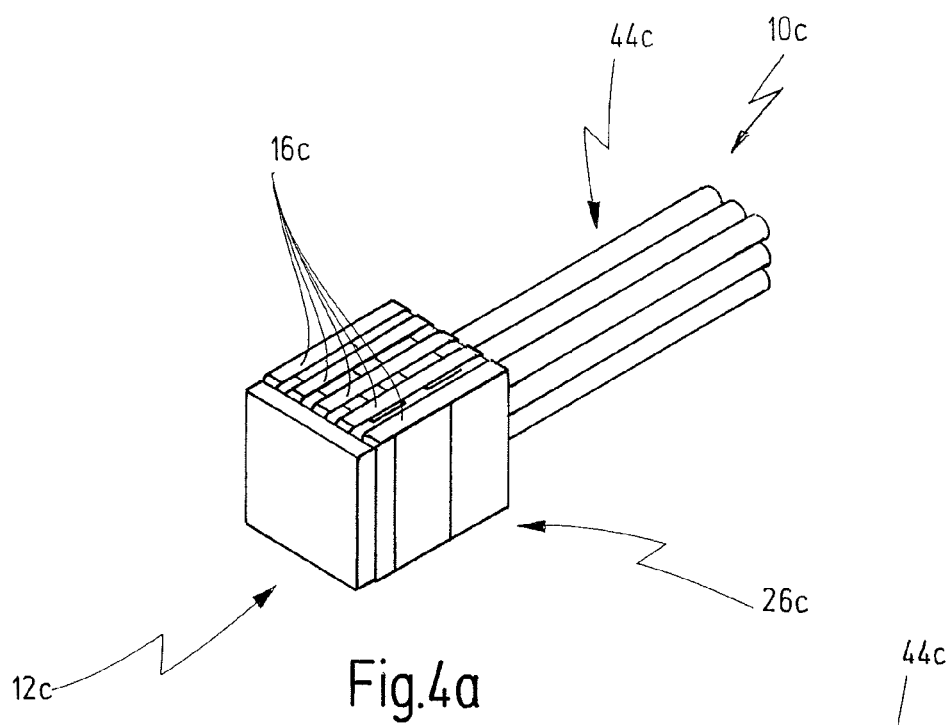
FIGS. 4a)+b) show another exemplary embodiment of an image pick-up module, FIG. 4a) showing a perspective side view of the image pick-up module in the assembled state and FIG. 4b) showing an exploded view of the individual components of the image pick-up module.

FIG. 4 shows another exemplary embodiment of an image pick-up module 10c, parts of the image pick-up module 10c which are the same as or comparable to corresponding parts of the image pick-up module 10 being provided with the same reference symbols supplemented by the letter c.

The image pick-up module 10c has a circuit board 26c which, like the image pick-up module 10b, is formed from two individual circuit boards 70, 72, both individual circuit boards 70, 72 being of U-shaped design. In this case too, a configuration with blind holes or the like may also be considered instead of a U-shaped configuration of the individual circuit boards 70, 72. It goes without saying that the grooves of the individual circuit boards may also be oriented in a manner rotated through 90° with respect to one another instead of being parallel to one another.

In contrast to the circuit board 26b, the individual circuit board 72, that is to say the last individual circuit board as seen from the image sensor 12c, assumes the function of contact-connecting the multi-core cable 44c. The cores of the multi-core cable 44c are contact-connected to the circuit board 26c, more precisely to the individual circuit board 72, but not on an underside 30c of the individual circuit board 72 which is remote from the image sensor 12c, as is the case in the image pick-up module according to DE 10 2004 056 946 A1, but rather on a side 74 facing the image sensor 12c. In this case, the cores of the cable 44c are guided through the individual circuit board 72 from the side 30c to the side 74, with the result that the contact-connection points 50c are closer to the image sensor 12c than the underside 30c. This also again results in the fact that the direct junction between the cable 44c and the underside 30c of the circuit board 26c is flexible at the point 52c.

Figure 4B:
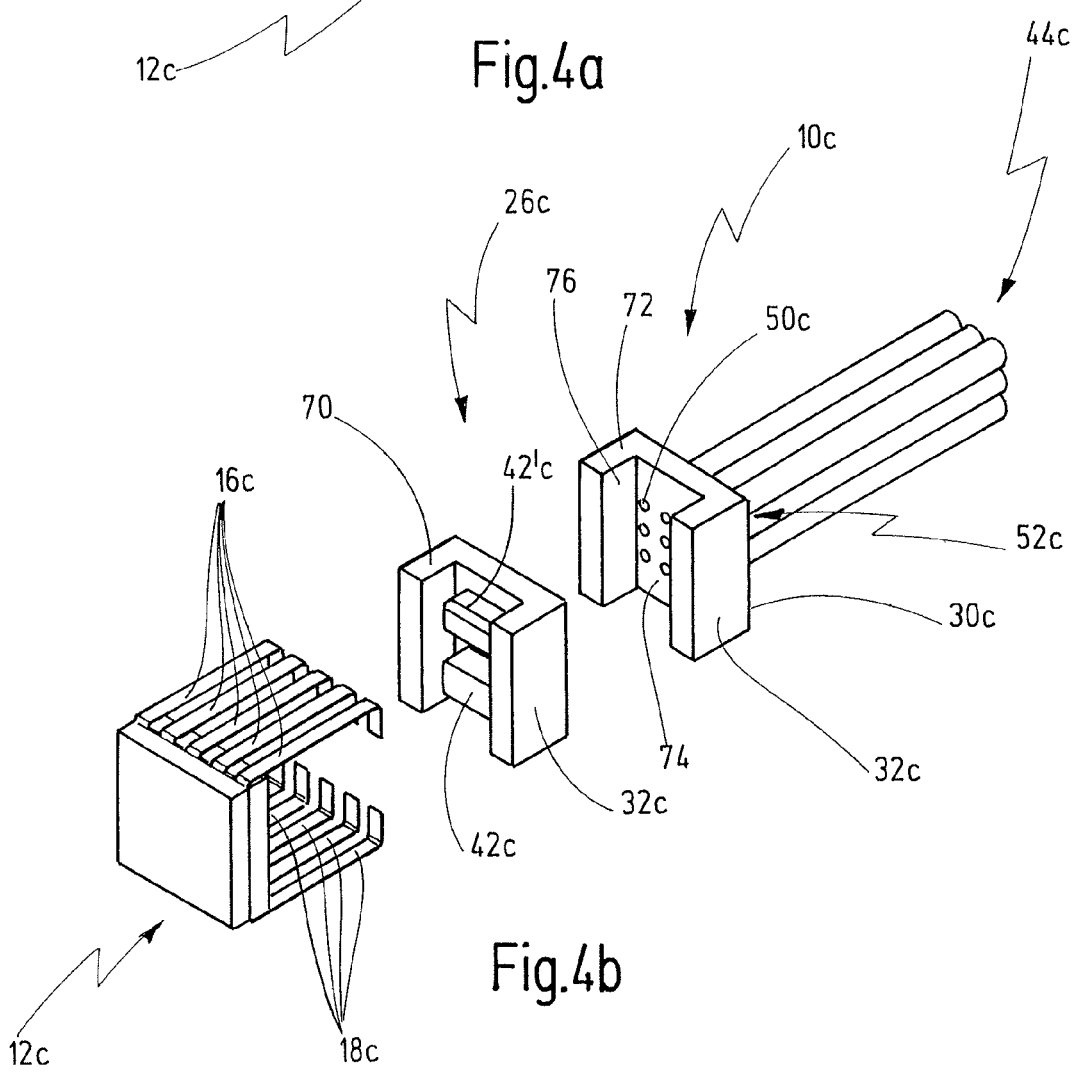

Whereas only the individual circuit board 70 according to FIG. 4b) has been provided with electronic components 42c, 42'c, the individual circuit board 72 can also additionally accommodate such electronic components in its groove-like depression 76, however.

For the rest, the image pick-up module 10c corresponds to the image pick-up module 10b.

Figure 5A:
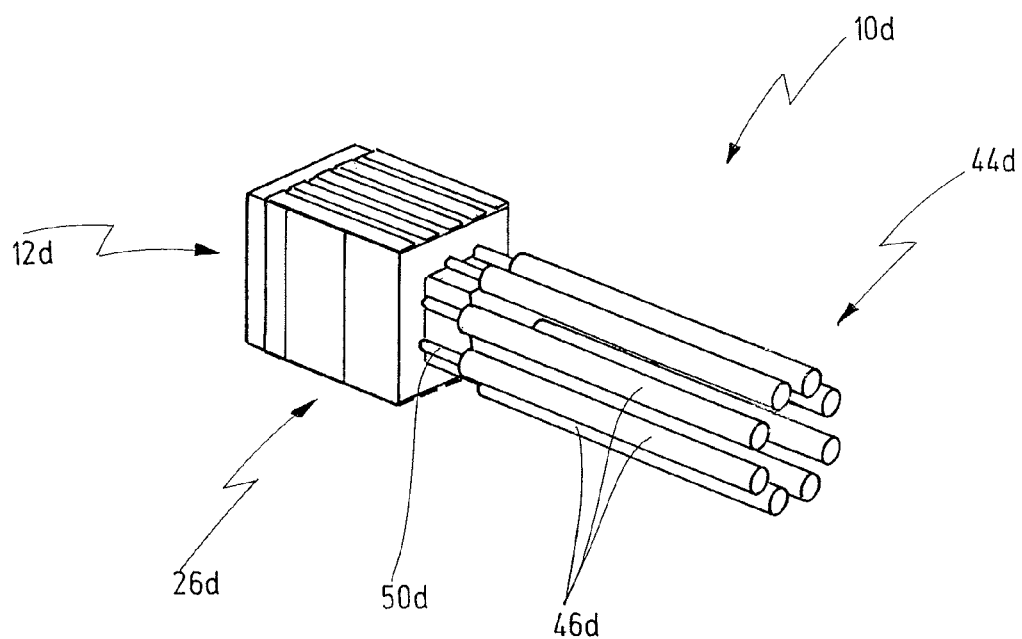
FIGS. 5a)+b) show another exemplary embodiment of an image pick-up module, FIG. 5a) showing a perspective side view of the image pick-up module in the assembled state and FIG. 5b) showing an exploded view of the individual components of the image pick-up module.
Figure 5B:
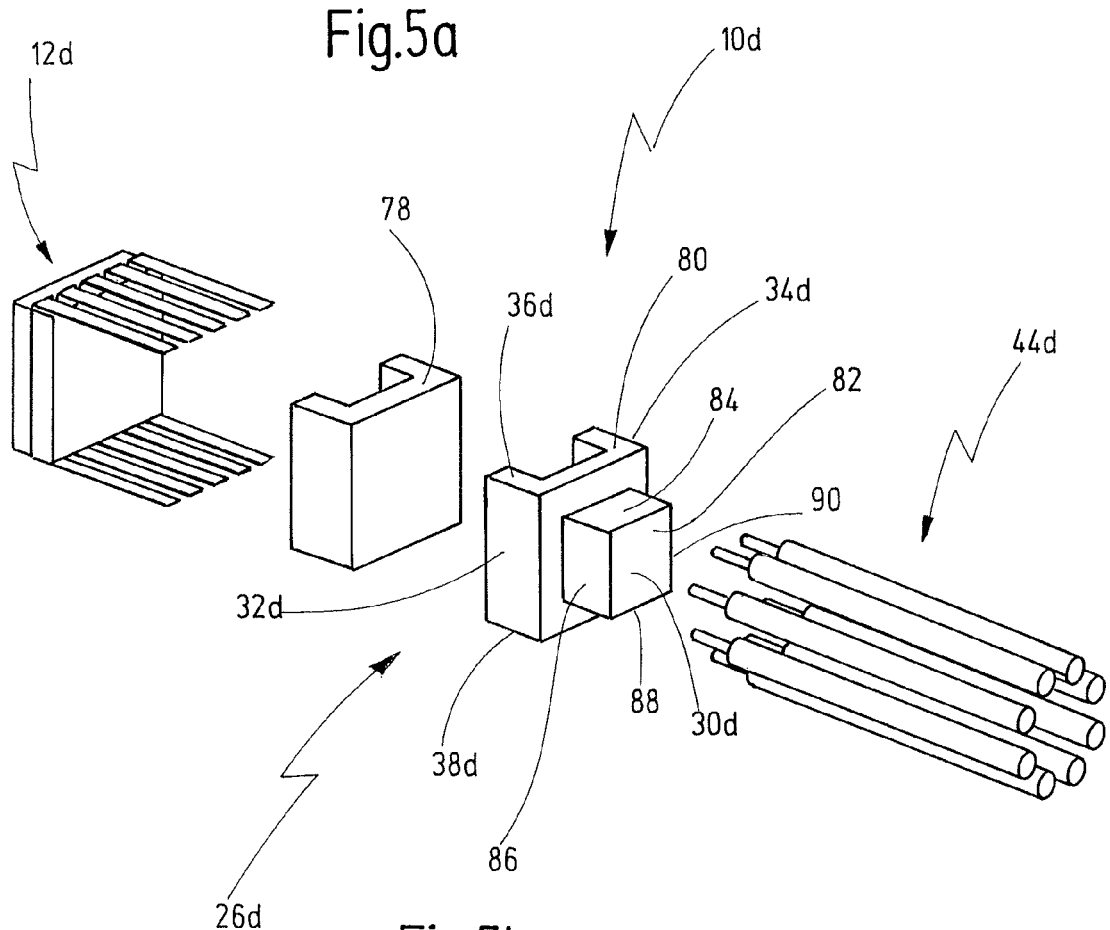

A further modification of the image pick-up module 10b in FIG. 3 is shown in FIG. 5 in the form of an image pick-up module 10d. Parts of the image pick-up module 10d which are the same as or comparable to corresponding parts of the image pick-up module 10 are provided with the same reference symbols supplemented by the letter d.

The image pick-up module 10d has a circuit board 26d which, like in the case of the two preceding exemplary embodiments, is formed from two individual circuit boards 78 and 80.

The individual circuit board 80, that is to say the last individual circuit board as seen from the image sensor 12d, is used as the cable terminal for contact-connecting the cores of the cable 44d. In contrast to the preceding exemplary embodiment, the individual circuit board 80 has a section 82 having longitudinal sides 84, 86, 88, 90, at least one of which, or all of which in the exemplary embodiment shown, is/are smaller than the longitudinal sides 32d, 34d, 36d, 38d of the remaining part of the circuit board 26d, with the result that the section 82 has a smaller cross-sectional dimension than the remaining part of the circuit board 26d and the image sensor 12d.

At least one of the longitudinal sides 84, 86, 88 and 90, or all of the longitudinal sides in the exemplary embodiment shown, is/are used to contact-connect the cores of the cable 44d, the contact-connection points 50d being at a distance from the underside 30d which is remote from the image sensor 12d in the direction of the image sensor 12d in this case too.

FIG. 6 illustrates another circuit board 26e which can be used as an individual circuit board in the exemplary embodiments according to FIGS. 3 to 5 instead of one of the individual circuit boards illustrated therein.

The circuit board 26a has throughplated holes 94, 96, 98, 100, 102, 104, 106 which extend from a first side 92 to a second side 94, the circuit board being able to have one or more recesses or milled-out areas 108 in the region of some throughplated holes, as in the case of the throughplated holes 98 and 100.

The throughplated holes 96 to 106 are lined with conductive material.

FIGS. 7 to 10 illustrate further image pick-up modules which are used to describe further aspects of the invention.

Figure 7A:
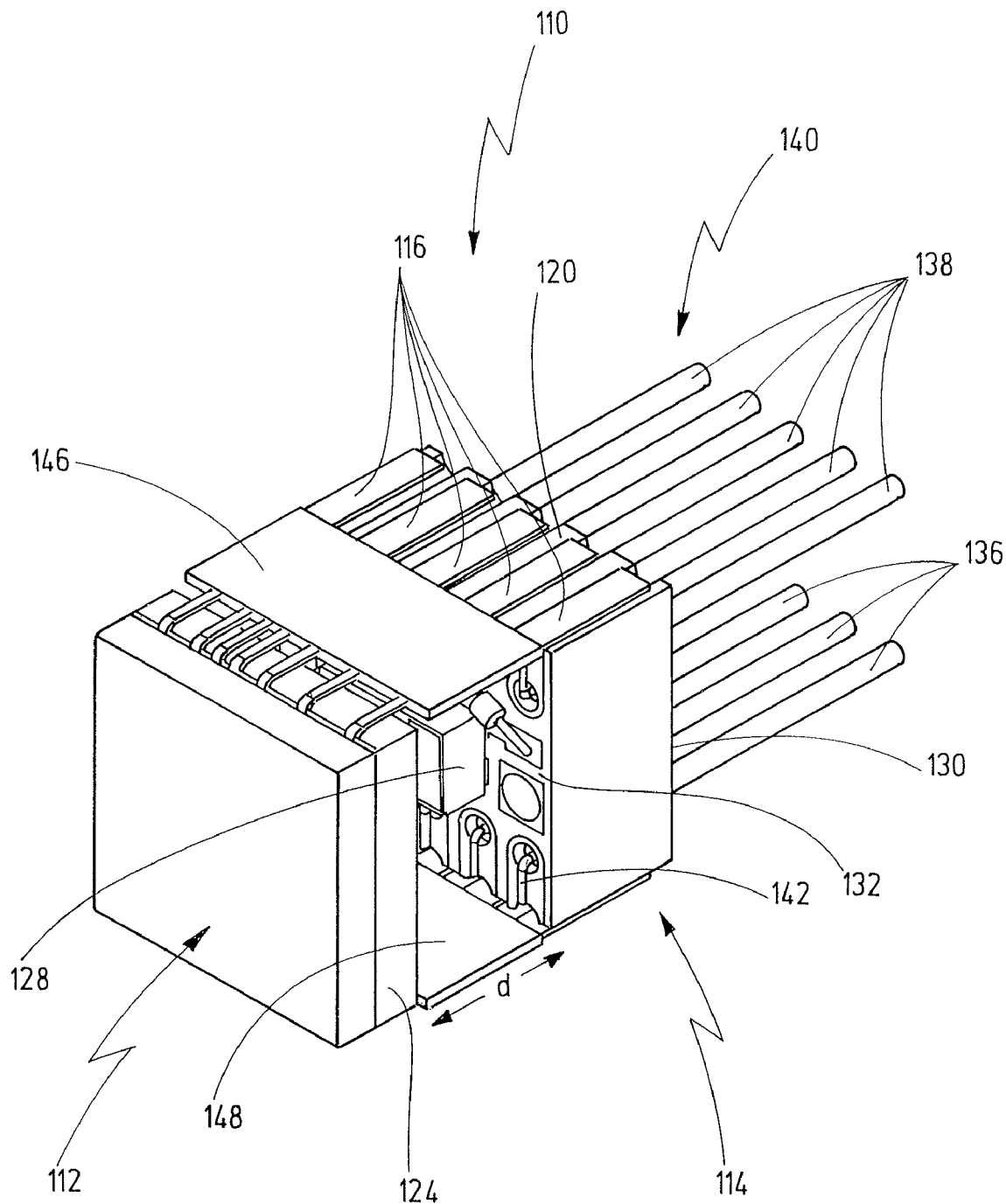
FIGS. 7a)-c) show another exemplary embodiment of an image pick-up module, FIG. 7a) showing a perspective view, FIG. 7b) showing a view of the underside, and FIG. 7c) showing a side view of the image pick-up module.
Figure 7B:
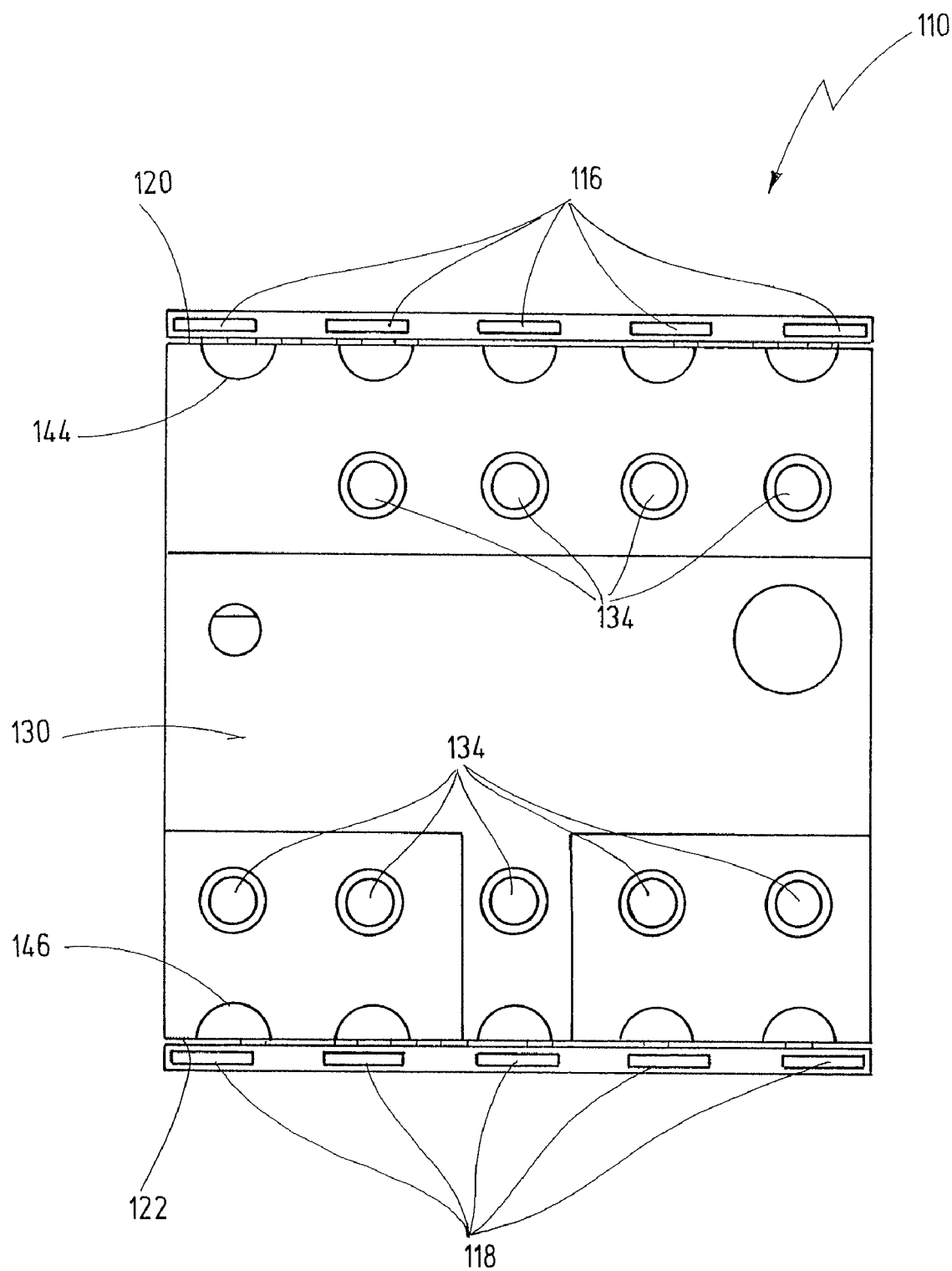
Figure 7C:
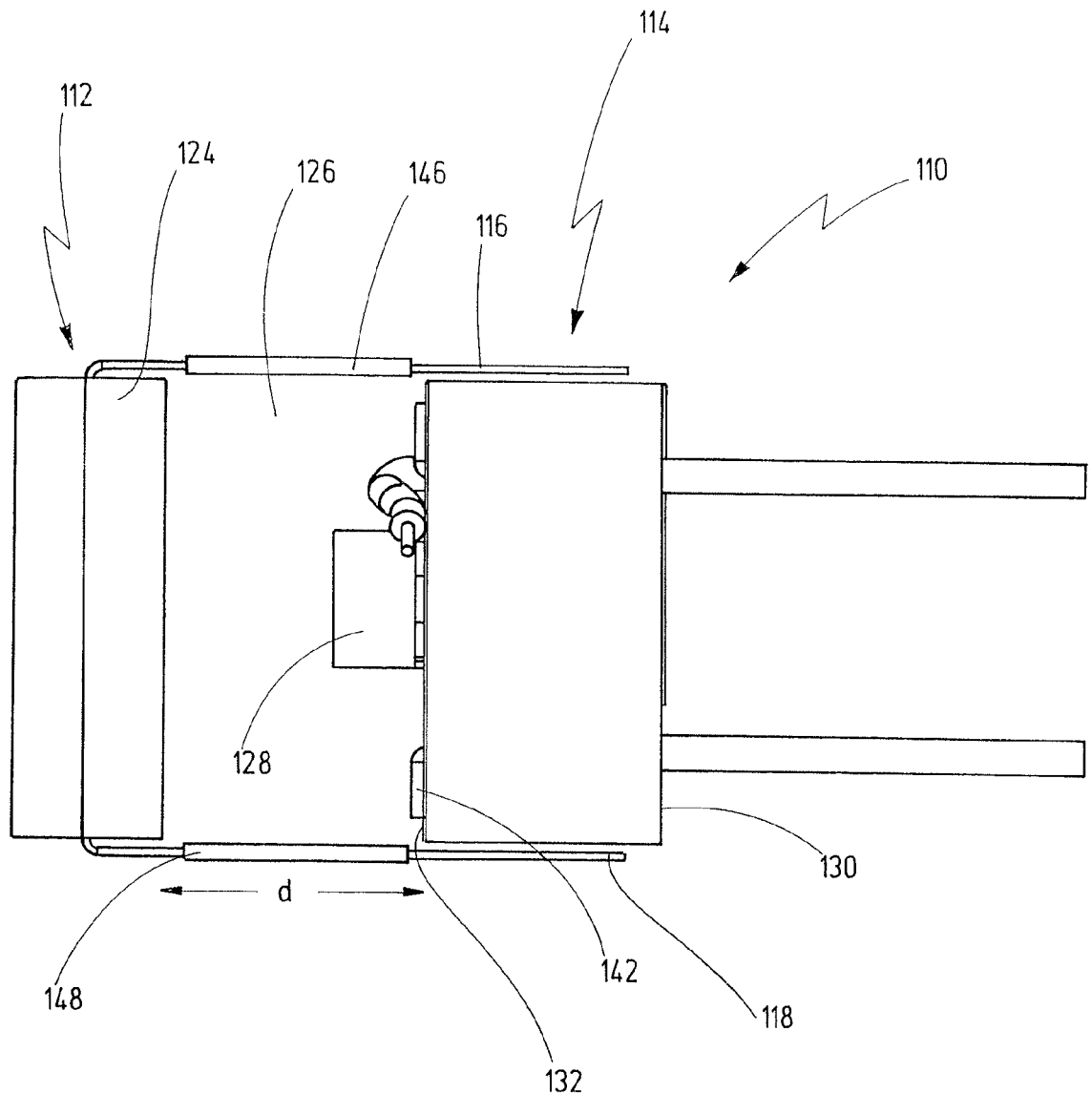

FIGS. 7a) to c) illustrate an image pick-up module 110 having an image sensor 112 and having a circuit board 114 to which a first row of contact fingers 116 and a second row of contact fingers 118 (cf. FIG. 7b)) of the image sensor 112 are electrically contact-connected, the contact fingers 116, 118 extending along longitudinal sides 120, 122 of the circuit board 114.

In the exemplary embodiment of the image pick-up module 110 shown, the circuit board 114 is of integral or single-part design in a manner comparable to the circuit board 26 or 26a. The circuit board 114 is arranged parallel to the image sensor 112 and has a length, as seen in the longitudinal direction, of approximately half the length of the circuit board 26 or 26a.

In contrast to the circuit board 26 or 26a, the circuit board 114 is at a distance d from the image sensor 112, more precisely from the basic body 124 of the latter, with the result that a free space 126 is present between the basic body 124 of the image sensor 112 and the circuit board 114, which space may optionally be filled with a curable filling composition which is electrically insulating. At least one electronic component 128 is arranged on the circuit board 114 and is electrically contact-connected to the latter in the space between the image sensor 112 and the circuit board 114.

In a manner comparable to the circuit board 26e in FIG. 6, the circuit board has holes 134 which start from its side or underside 130 which is remote from the image sensor 112, extend to the side or top side 132 which faces the image sensor 112 and through which cores 136, 138 of a multi-core flexible cable 140 are guided, the individual cores being contact-connected to the circuit board 114 on that side 132 of the circuit board 114 which faces the image sensor 112. The contact-connection points are thus likewise again closer to the image sensor 112 than the underside 130 of the circuit board 114 which is remote from the image sensor 112, as shown in FIG. 7a) for a contact-connection point 142 of one of the cores 136, for example.

As already mentioned, the contact fingers 116, 118 of the image sensor 112 are arranged along the longitudinal sides 120, 122 of the circuit board 114 and are electrically contact-connected to the circuit board 114 on these two longitudinal sides 120, 122. A plurality of elongate contacts 144 (a total of ten in the exemplary embodiment shown) which are arranged so as to be recessed are arranged on the longitudinal sides 120, 122 of the circuit board 114, extend in the longitudinal direction of the circuit board 114 and extend from the underside 130 to the top side 132. The contact fingers 116 and 118 are electrically contact-connected to these elongate contacts 144, 146.

The contact fingers 116 and 118 are respectively stabilized by a plate 146 and 148, in particular in the region in which the contact fingers 116, 118 bridge the free space 126 between the circuit board 114 and the image sensor 112. The plates 146, 148 are made from electrically insulating material.

Figure 8A:
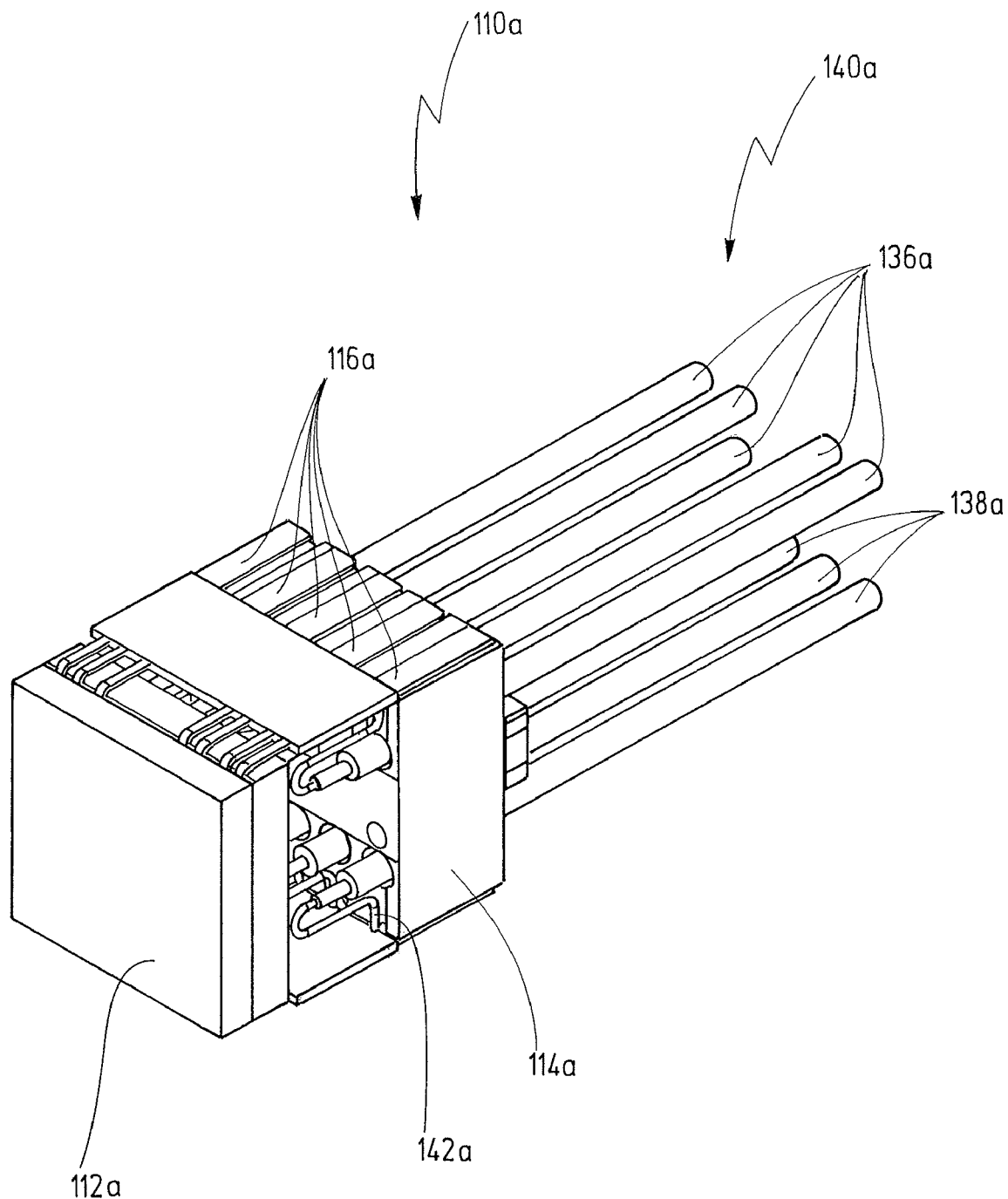
FIGS. 8a)-c) show another exemplary embodiment of an image pick-up module, FIG. 8a) showing a perspective view, FIG. 8b) showing a view of the underside of the image pick-up module, and FIG. 8c) showing a side view of the image pick-up module.
Figure 8B:
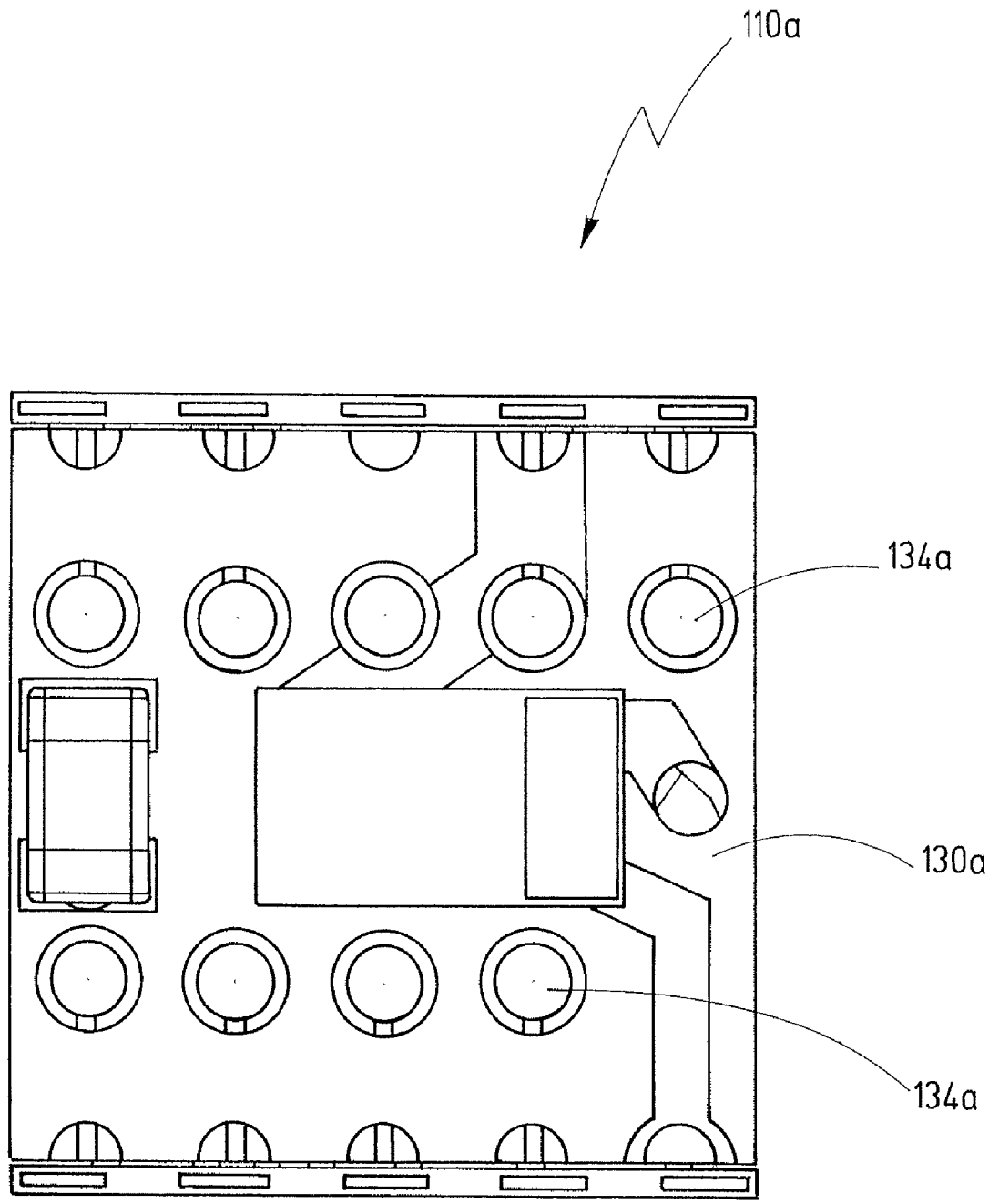
Figure 8C:
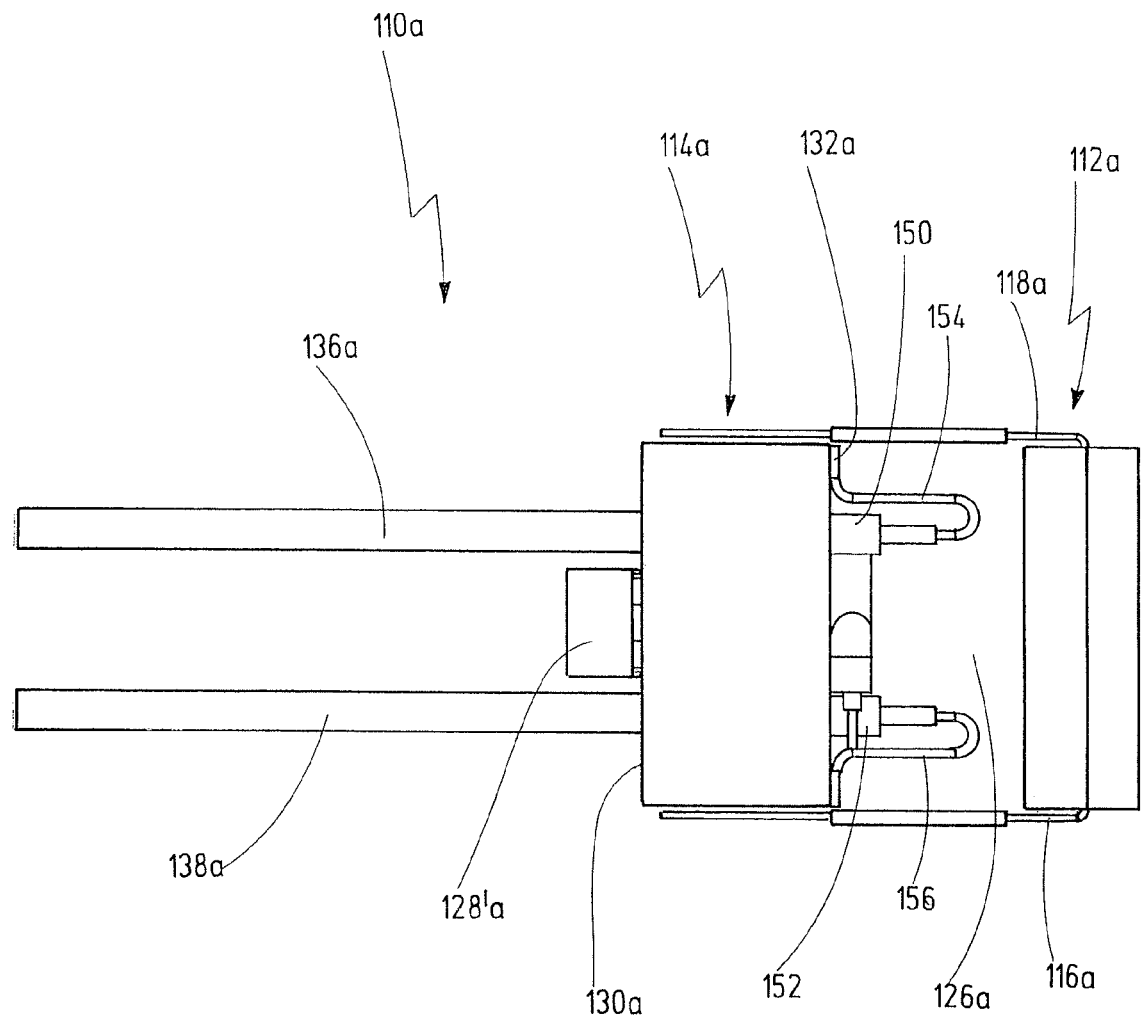

FIGS. 8a) to c) illustrate a modification of the image pick-up module 110 in the form of an image pick-up module 110a. Parts of the image pick-up module 110a which are the same as or comparable to corresponding parts of the image pick-up module 110 are provided with the same reference symbols supplemented by the letter a.

The image pick-up module 110a has a circuit board 114a which is at a distance from the image sensor 112a, as in the previous exemplary embodiment, with the result that a free space 126a is present between the image sensor 112a and the circuit board 114a and is optionally filled with an electrically insulating curable filling composition.

In contrast to the previous exemplary embodiment, at least one electronic component 128'a is also arranged on the underside 130a of the circuit board 114a, which is remote from the image sensor 112a, and is electrically contact-connected to said circuit board.

The cores 136a and 138a of the multi-core cable 140a are again guided through the circuit board 114a through holes 134a and are contact-connected to the circuit board 114a on a top side 132a.

In comparison with the previous exemplary embodiment, the cores 136a and 138a are guided through the circuit board 114a to such an extent that their sheaths, in particular screens 150 and 152, protrude from the top side 132a of the circuit board 114a, the exposed ends 154 and 156 being bent through 180° from the longitudinal direction and their outermost ends being electrically contact-connected to the circuit board 114a on the top side 132a.

It goes without saying that electrical components may also be arranged on the top side 132a of the circuit board 114a and may be contact-connected to the circuit board 114a.

Figure 9A:
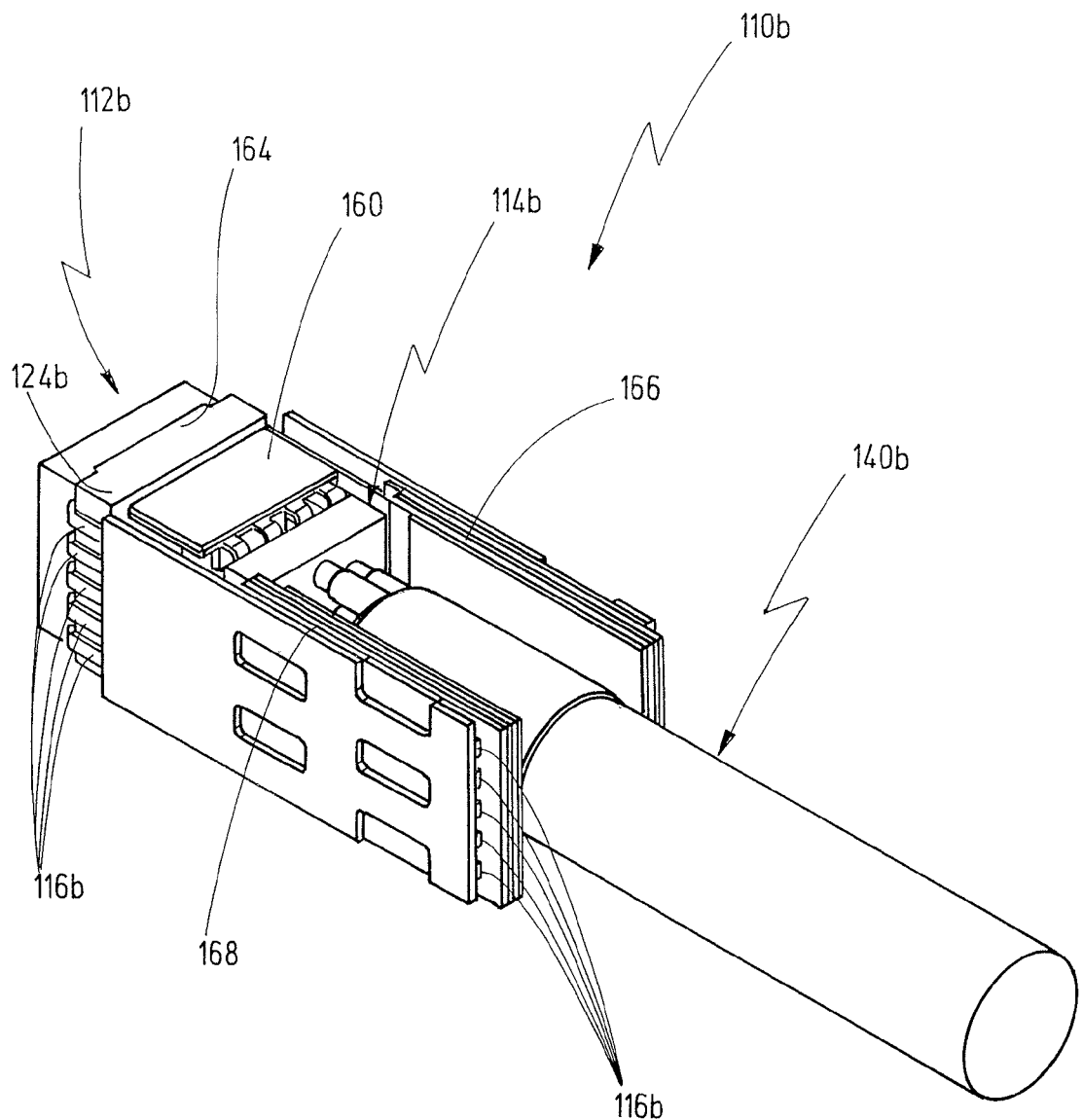
FIGS. 9a)+b) show another exemplary embodiment of an image pick-up module, FIG. 9a) showing a perspective view and FIG. 9b) showing a side view.
Figure 9B:
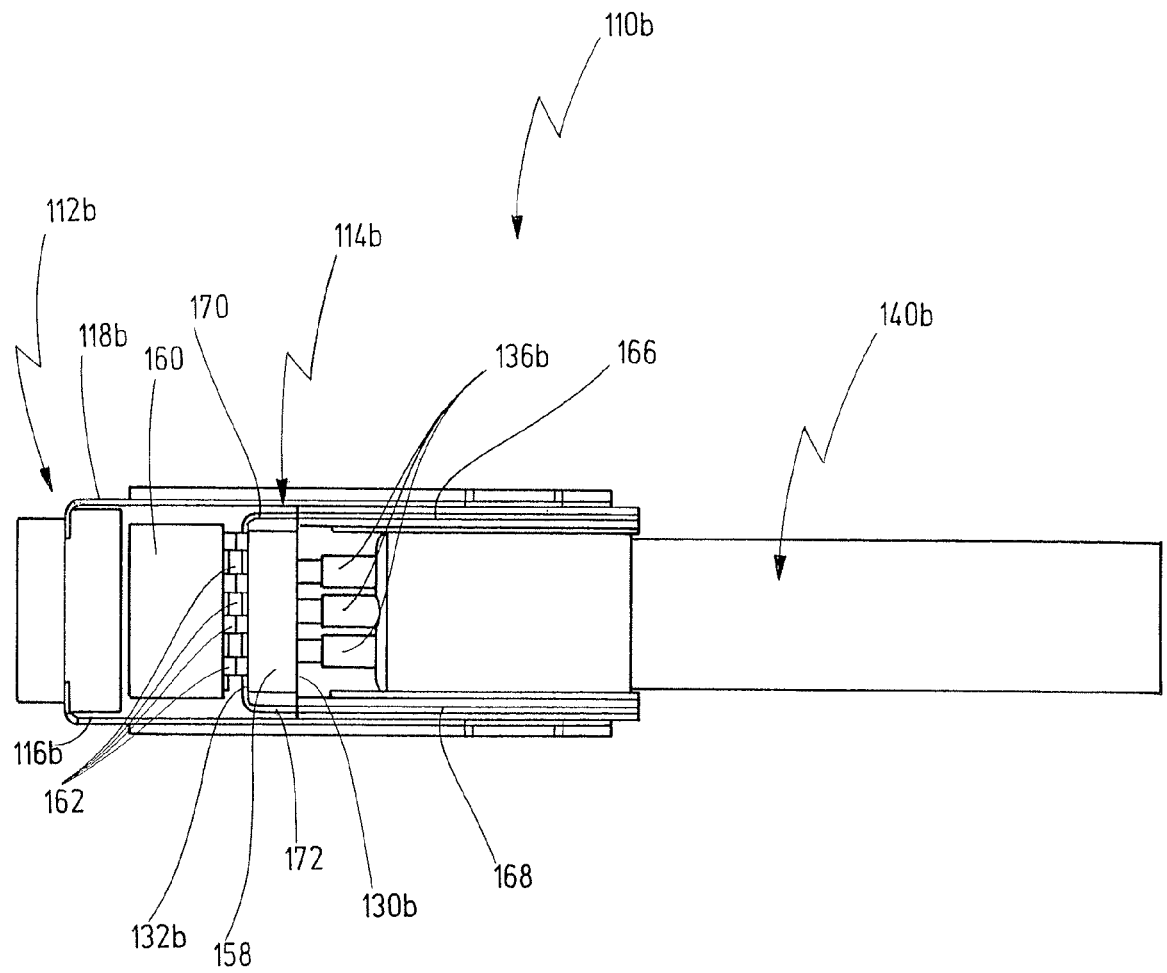
Figure 10A:
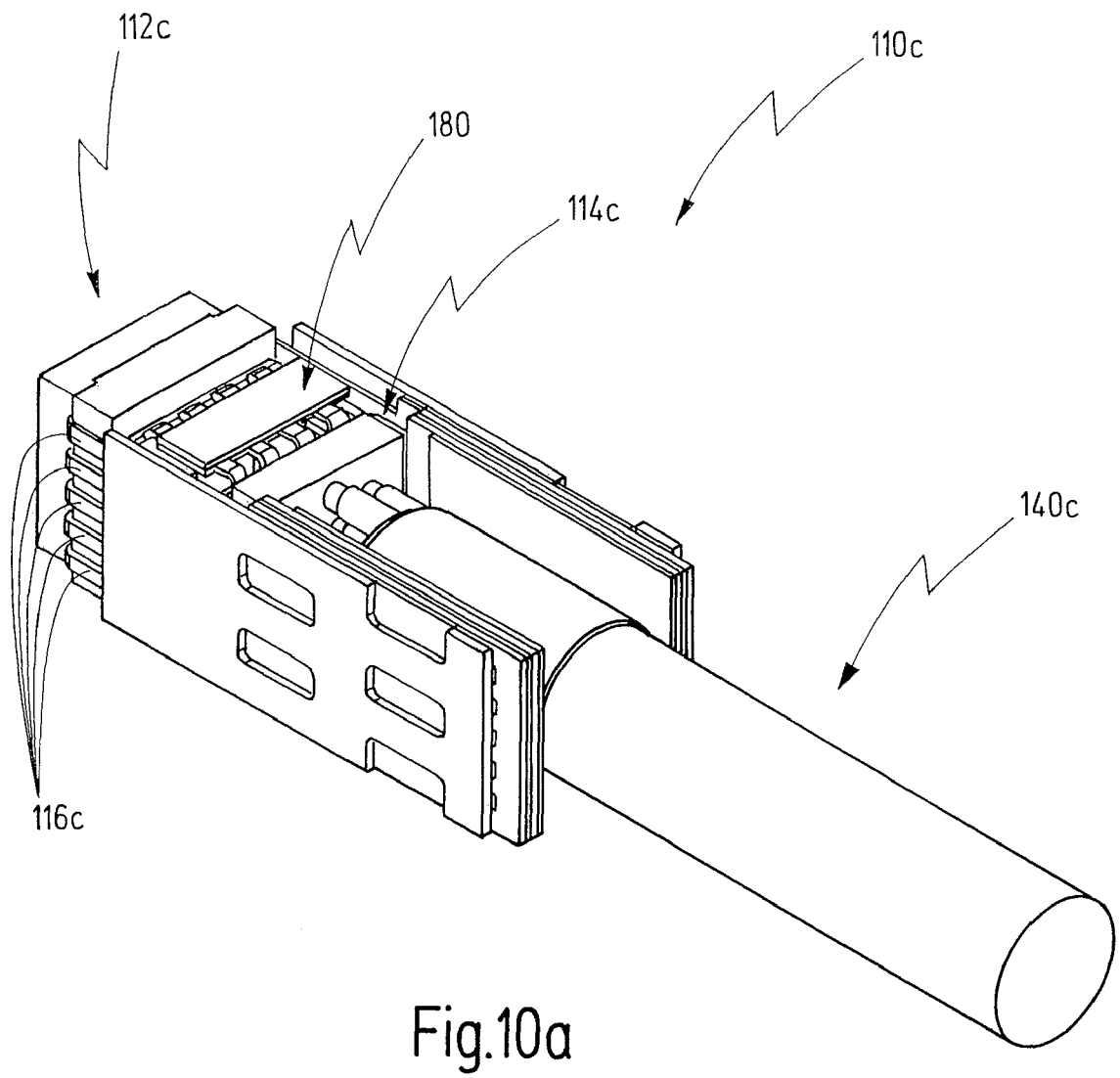
FIGS. 10a)+b) show another exemplary embodiment of an image pick-up module, FIG. 10a) showing a perspective view and FIG. 10b) showing a side view.
Figure 10B:
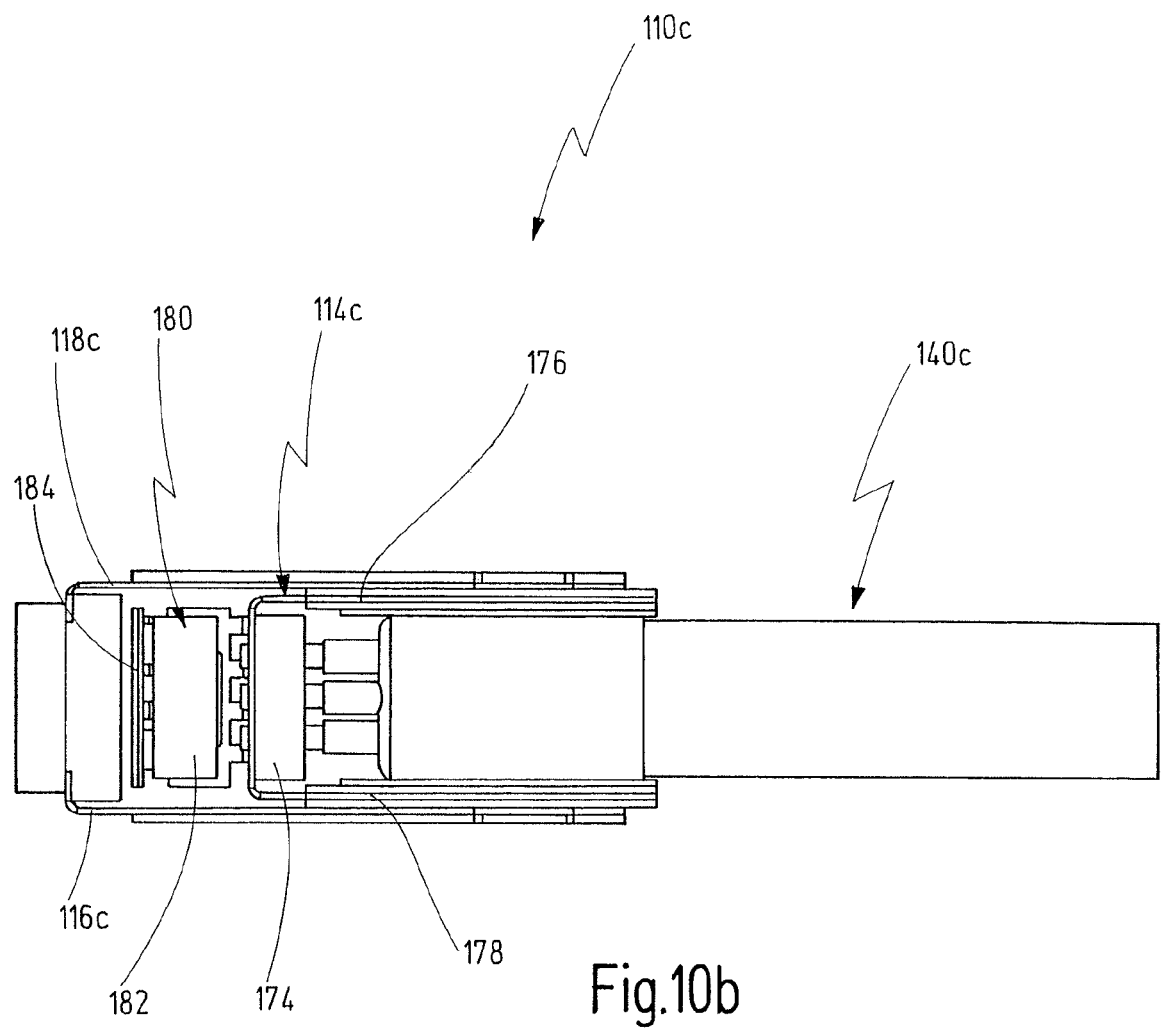

FIGS. 9 and 10 illustrate two further modifications of the image pick-up module 110.

FIGS. 9a) and b) show an image pick-up module 110b having the main components of an image sensor 112b, a circuit board 114b and a flexible multi-core cable 140b.

In contrast to the circuit board 114 or 114a, the circuit board 114b is of multi-part construction.

The circuit board 114b has a rigid base board 158 whose function in this case is to contact-connect cores 136b of a multi-core flexible cable 140b. The cores 136b are again preferably guided through holes (not illustrated in any more detail) from the underside 130b to the top side 132b of the base board 158 and are contact-connected to the base board 158 on the top side 132b.

The base board 158 preferably does not have any electronic components. Rather, in order to accommodate electronic components, the circuit board 114b has at least one further circuit board part 160 which is flexibly connected to the base board 158, to be precise by means of conductors or conductor tracks 162. The further circuit board part 160 is in the form of a thin plate and extends perpendicular to the image sensor 112b in the space between the base board 158 and the image sensor 112b.

The circuit board part 160 extends approximately in the form of an extension of a longitudinal side 164 of the image sensor 112a or the basic body 124a of the latter and may have, on its inner side (not illustrated), one or more electronic components which are electrically contact-connected to the circuit board part 160. A further circuit board part of this type may also be arranged parallel to the circuit board part 160 on the opposite longitudinal side.

Two further circuit board parts 166 and 168 are flexibly connected to the base board 158, to be precise by means of conductors 170 and 172.

The circuit board parts 166 and 168 likewise run transversely to the image sensor 112b and are arranged on that side of the base board 158 on which the contact fingers 116b and 118b also run but run past the base board 158 and are contact-connected to the circuit board parts 166 and 168.

The circuit board parts 166 and 168 are used, inter alia, to partially enclose the multi-core cable 140b but without impairing the flexibility of the cable 140b.

FIGS. 10a) and b) illustrate a modification of the image pick-up module 110b in the form of an image pick-up module 110c. Parts of the image pick-up module 110c which are the same as or comparable to corresponding parts of the image pick-up module 110 are provided with the same reference symbols supplemented by the letter c.

Only the differences to the image pick-up module 110c are described below.

The image pick-up module 110c has a circuit board 114c which, like in the previous exemplary embodiment, has a base board 174, two circuit board parts 176, 178 which lead from the base board 174 to the proximal end transversely to the image sensor 112c, and a circuit board part 180 which leads away from the base board 174 to the distal end and extends transversely to the image sensor 112c.

The circuit board part 180 has a first section 182 and a second section 184 which adjoins the latter, the sections 182 and 184 running perpendicular to one another and being connected to one another in an electrically conductive and flexible manner, the section 182 extending perpendicular to the base board 174 and the section 184 extending parallel to the base board and parallel to the image sensor 112c.

Electronic components may be contact-connected both to the section 182 and to the section 184.

In the exemplary embodiments according to FIGS. 9 and 10, the base board and the associated circuit board parts may be produced from a circuit board blank, the base board having a greater material thickness than the further circuit board parts, for example as a result of subsequent addition of a carrier material to the base board or as a result of removal of carrier material from the circuit board parts.

In all of the exemplary embodiments described above, the circuit boards or individual circuit boards, for example the circuit boards 26, 26a-e, 114, 114a-c, may be in the form of multilayer circuit boards. In the case of the circuit board 26 for example, the latter may be constructed from a plurality of layers, with the result that conductor tracks also run inside the circuit board body.

What is claimed is:

1. An image pick-up module, comprising an electronic image sensor,
  a rigid circuit board to which said image sensor is electrically contact-connected, said image sensor and said circuit board being arranged approximately parallel to one another, and
  a flexible multi-core cable leading from said circuit board in direction away from said image sensor, wherein cores of said multi-core cable are electronically contact-connected to said circuit board at contact-connection points on said circuit board which are closer to said image sensor than a side of said circuit board which is facing away from said image sensor, said contact-connection points of said cores are situated on a side of said circuit board which faces said image sensor, and said cores together with their sheaths are guided through said circuit board from said side which is facing away from said image sensor to said side which faces said image sensor.

2. The image pick-up module of claim 1, wherein said circuit board is at a distance from said image sensor so that there is a space between said image sensor and said circuit board.

3. The image pick-up module of claim 2, wherein at least one electronic component is arranged in said space between said image sensor and said circuit board.

4. The image pick-up module of claim 2, wherein said space between said circuit board and said image sensor is filled with a curable electrically insulating filling material.

5. The image pick-up module of claim 1, wherein said image sensor has a plurality of contact fingers that are arranged in at least one row, and said contact fingers of said image sensor are contact-connected on at least one longitudinal side of said circuit board on which elongate contacts which are arranged so as to be recessed are provided.

* * * * *